US012285738B2

(12) United States Patent
Sun

(10) Patent No.: US 12,285,738 B2
(45) Date of Patent: Apr. 29, 2025

(54) MODULATION OF GLUCOSE BIOACCESSIBILITY WITH SUPERABSORBENT MATERIALS

(71) Applicant: SIMEON INVESTMENT, INC., Arcadia, CA (US)

(72) Inventor: Lijun Sun, La Canada Flintridge, CA (US)

(*) Notice: Subject to any disclaimer, the term of this patent is extended or adjusted under 35 U.S.C. 154(b) by 842 days.

(21) Appl. No.: 17/401,179

(22) Filed: Aug. 12, 2021

(65) Prior Publication Data

US 2021/0370269 A1 Dec. 2, 2021

Related U.S. Application Data

(60) Continuation-in-part of application No. 17/339,416, filed on Jun. 4, 2021, now Pat. No. 11,911,744, which is a division of application No. 16/807,004, filed on Mar. 2, 2020, now Pat. No. 11,045,786, which is a continuation of application No. PCT/US2019/046077, filed on Aug. 10, 2019.

(60) Provisional application No. 62/717,644, filed on Aug. 10, 2018.

(51) Int. Cl.
*B01J 20/24* (2006.01)
*A61K 31/736* (2006.01)
*B01J 20/30* (2006.01)

(52) U.S. Cl.
CPC .......... *B01J 20/24* (2013.01); *A61K 31/736* (2013.01); *B01J 20/3021* (2013.01); *B01J 20/3078* (2013.01)

(58) Field of Classification Search
CPC ..... A61K 31/736; B01J 20/24; B01J 20/3021; B01J 20/3078
See application file for complete search history.

(56) References Cited

U.S. PATENT DOCUMENTS

| 4,781,838 A | 11/1988 | Crassous et al. |
| 5,409,703 A | 4/1995 | McAnalley et al. |
| 5,545,414 A | 8/1996 | Behr et al. |
| 6,271,278 B1 | 8/2001 | Park et al. |
| 7,157,431 B2 | 1/2007 | McAnalley et al. |
| 8,128,977 B2 | 3/2012 | Anfinsen et al. |
| 8,465,785 B2 | 6/2013 | Anfinsen et al. |
| 8,859,701 B2 | 10/2014 | Loick et al. |
| 9,457,048 B2 | 10/2016 | Davis et al. |
| 9,492,473 B2 | 11/2016 | von Maltzahn et al. |
| 9,855,294 B2 | 1/2018 | Heshmati et al. |
| 9,867,847 B2 | 1/2018 | Davis et al. |
| 9,901,595 B2 | 2/2018 | von Maltzahn et al. |
| 10,172,374 B2 | 1/2019 | Makita et al. |
| 10,272,155 B2 | 4/2019 | Elenko et al. |
| 10,584,183 B2 | 3/2020 | Sannino et al. |
| 10,695,363 B2 | 6/2020 | Rescigno et al. |
| 10,953,038 B2 | 3/2021 | Heshmati et al. |
| 2003/0224022 A1 | 12/2003 | Nussinovitch |
| 2005/0118326 A1 | 6/2005 | Anfinsen et al. |
| 2005/0250734 A1 | 11/2005 | Moreyra et al. |
| 2006/0093720 A1 | 5/2006 | Tatz |
| 2007/0104754 A1 | 5/2007 | Sterling et al. |
| 2012/0052151 A1 | 3/2012 | Sannino et al. |
| 2014/0276330 A1 | 9/2014 | Costa |
| 2015/0125568 A1 | 5/2015 | James |
| 2015/0196641 A1 | 7/2015 | Elenko et al. |
| 2015/0282510 A1 | 10/2015 | Makita et al. |
| 2015/0366898 A1 | 12/2015 | Heshmati et al. |
| 2015/0366989 A1 | 12/2015 | Liang et al. |
| 2016/0113953 A1 | 4/2016 | Gannedahl |
| 2016/0361351 A1 | 12/2016 | Davis et al. |
| 2017/0319616 A1* | 11/2017 | Lim ............... A61K 31/723 |
| 2018/0289043 A1 | 10/2018 | Sannino et al. |
| 2019/0290675 A1 | 9/2019 | Gibson et al. |
| 2019/0373939 A1 | 12/2019 | Liu |
| 2020/0009168 A1 | 1/2020 | von Maltzahn et al. |
| 2020/0054572 A1 | 2/2020 | Matthiasson et al. |
| 2020/0165406 A1 | 5/2020 | Fitzpatrick et al. |
| 2021/0000896 A1 | 1/2021 | Mazoyer et al. |
| 2021/0038871 A1 | 2/2021 | Zhao et al. |
| 2021/0113596 A1 | 4/2021 | von Maltzahn et al. |

FOREIGN PATENT DOCUMENTS

| JP | H09234004 A | 9/1997 |
| JP | 2003518008 A | 6/2003 |
| JP | 2005185211 A | 7/2005 |
| JP | 2012080806 A | 4/2012 |

(Continued)

OTHER PUBLICATIONS

USPTO; International Search Report and Written Opinion issued in Application No. PCT/US19/46077; dated Nov. 13, 2019; 10 pages.
Ni, et al.; "The Control of Ice Crystal Growth and Effect on Porous Structure of Konjac Glucomannan-Based Aerogels"; International Journal of Biologial Macromolecules; 2016; vol. 92; pp. 1130-1135.
Takei, et al.; "Autoclavable physically-crosslinked chitosan cryogel as a wound dressing"; Journal of Bioscience and Bioengineering; 2017; vol. 125; No. 4; pp. 490-495.
"Gelesis 100 Reduces Insulin Resistance in GLOW Obesity Trial;" Webpage located at: https://medtech.pharmaintelligence.informa.com/MT124859/Gelesis100-Reduces-Insulin-Resistance-in-GLOW-Obesity-Trial; accessed on Mar. 29, 2019.

(Continued)

*Primary Examiner* — Pancham Bakshi

(57) ABSTRACT

A treatment for reducing glucose bioaccessibility can include providing a superabsorbent material that includes a porous network structure formed from a mixture of a plurality of water soluble polysaccharides that are not chemically crosslinked together. The superabsorbent material can be administered to a subject in an effective amount to reduce glucose bioaccessibility in the subject. In some aspects, the treatment for reducing glucose bioaccessibility with the superabsorbent material retains a substantially unaltered fatty acid bioaccessibility and/or retains a substantially unaltered protein bioaccessibility.

19 Claims, 13 Drawing Sheets

(56) References Cited

FOREIGN PATENT DOCUMENTS

| | | |
|---|---|---|
| WO | 20010001950 A1 | 1/2001 |
| WO | 20010087365 A2 | 11/2001 |
| WO | 2004022074 A1 | 3/2004 |
| WO | 2005036971 A1 | 4/2005 |
| WO | 2010059725 A1 | 5/2010 |
| WO | 2014202997 A2 | 12/2014 |
| WO | 2015011988 A1 | 1/2015 |
| WO | 2015196054 A1 | 12/2015 |
| WO | 2016085322 A1 | 6/2016 |
| WO | 2018106845 A1 | 6/2018 |

OTHER PUBLICATIONS

"Gelesis Presents Pre-Clinical Data Suggesting Proprietary Hydrogel (GS300 Prototype) Reverses the Damage to the Intestines Induced by a High Fat Diet;" Website located at: https://www.gelesis.com/2020/11/13/gelesis-presents-pre-clinical-data-suggesting-proprietary-hydrogel-gs300-prototype-reverses-the-damage-to-the-intestines-induced-by-a-high-fat-diet/; accessed on Nov. 13, 2020.

"Puretech Big-Gelesis (Proprietary Hydrogel Technology) (PLENITY, Gelesis200, GS300, GS400, GS500);" Webpage located at: https://puretech.red-hill.com/puretech-pipeline/details/hydrogel-platform-technology-for-gi-related-diseases; accessed on May 19, 2021.

"Puretech Big-Giving Life to Science;" Webpage located at: https://puretechhealth.com/programs/details/gelesis-product-candidates; accessed on May 20, 2021.

Albillos et al., "The gut-liver axis in liver disease: Pathophysiological basis for therapy," J. Hepatol. 2020, 72, 558-77.

Bu et al., "The hydration mechanism and hydrogen bonding structure of 6-carboxylate chitooligosaccharides superabsorbent material prepared by laccase/TEMPO oxidation system," Carbohydr. Polym. 2018, 188, 151-158.

Entry for Agar, emedicinehealth.com 2016.

Functional Food Processing Technology, 1st ed.; Shimin Li ed.; China Light Industry Press, 2003; pp. 18-20.

Guo et al., "Effects of superabsorbent polymers on the abundances of antibiotic resistance genes, mobile genetic elements, and the bacterial community during swine manure composting," Bioresour. Technol. 2017, 244 (Pt 1), 658-63.

Klop et al., "Dyslipidemia in obesity: mechanisms and potential targets," Nutrients 2013, 5, 1218-40.

Liu et al., "Ingestible hydrogel device," Nat. Commun. 2019, 10, 493.

Rhim et al., "Mechanical and water barrier properties of agar/κ-carrageenan/konjac glucomannan ternary blend biohydrogel films," Carbohydr. Polym. 2013, 96, 71-81.

Silverstri et al., "GELESIS Superabsorbent Hydrogel Prevents Hepatic Steatosis and Insulin Resistance in High Fat Diet-Induced NAFLD Pre-Clinical Model;" In The International Liver Congress 2019 (EASL 2019); Vienna, Austria, 2019.

Takei et al., "Autoclavable physically-crosslinked chitosan cryogel as a wound dressing," J. Biosci. Bioeng. 2018, 125, 490-5.

Ni et al., "The control of ice crystal growth and effect on porous structure of konjac glucomannan-based aerogels," Int. J. Biol. Macromol. 2016, 92, 1130-5.

* cited by examiner

MODULATION OF GLUCOSE BIOACCESSIBILITY WITH SUPERABSORBENT MATERIALS

CROSS-REFERENCE TO RELATED APPLICATIONS

This application is a continuation-in-part of U.S. application Ser. No. 17/339,416 filed Jun. 4, 2021, which is a divisional of U.S. application Ser. No. 16/807,004 filed Mar. 2, 2020, which is a continuation of International Patent Application No. PCT/US2019/046077 filed Aug. 10, 2019, which claims the benefit of U.S. Provisional Patent Application No. 62/717,644 filed Aug. 10, 2018, which applications are incorporated herein by specific reference in their entirety.

BACKGROUND

Field

The present disclosure relates to use of superabsorbent materials in a treatment for modulating glucose bioavailability.

Description of Related Art

Insulin is a glucose regulating hormone that allows glucose to enter cells and reduce blood glucose levels. The pancreas releases insulin when glucose is consumed in the diet or generated in the gut from consumed carbohydrates. Poor health and overeating foods, such as those resulting in high glucose availability, can lead to irregular insulin levels, obesity, and diabetes. During insulin resistance, the normal amount of insulin does not have the same effect on glucose transport and blood sugar levels. With high blood glucose levels, higher insulin amounts are released and the subject experiences higher insulin levels in an attempt to overcome the high blood glucose level. Often, high glucose intake is related to obesity and diabetes, which can be related to higher insulin levels. Therefore, it may be advantageous to reduce glucose intake and absorption.

Obesity and diabetes may be caused by a malfunction in the metabolism or absorption of digestible carbohydrates. This results in high levels of blood glucose and insulin. High amounts of insulin promote the production and storage of fat. High average levels of glucose (>180 mg/dL) in the blood stream will bind to organ proteins (glycosylation) resulting in the deterioration of organ function.

It can be beneficial for people with diabetes and people who are overweight or obese to avoid foods with a high glycemic response, such as those that result in abnormally high levels of blood glucose after ingestion. In many instances, diabetics and other people controlling their weight consume foods having a lower blood glucose response (e.g., glycemic response or index), which results in a slower rate of glucose release into the blood. Slowing the rate of release of glucose into the blood reduces the risk of both high blood glucose (hyperglycemia) and low blood glucose (hypoglycemia). A problem in meeting this goal is experienced when large quantities of foods high in digestible carbohydrates are consumed. Such foods typically include bakery products, pastas, rice, snacks, potatoes, sauces, gravies, beverages, soups, casseroles, and candies. These foods, containing high levels of digestible starch and/or sugars, especially when eaten in excess can significantly increase 2-hour postprandial blood glucose levels.

Previously, various strategies have been used for modulating glucose absorption. Crosslinked carboxymethylcellulose has been used for modulating blood glucose levels (U.S. 2015/0366898; U.S. Pat. No. 10,953,038). Additionally, reduced carbohydrate foods have been suggested (U.S. Pat. No. 8,128,977). Swellable polymeric hydrogels have been suggested for glycemic control (U.S. 2012/0052151). However, research continues for improvements in regulating a proper glucose bioaccessibility.

While there have been proposed treatments for reducing glucose intake or absorption, overconsumption of glucose and glucose-generating foods continues to be problematic. Accordingly, there is still a need in the art to develop an improved dietary product that can be used in a treatment for reducing glucose absorption or bioavailability in a subject in need thereof.

SUMMARY

In some embodiments, a treatment for reducing glucose bioaccessibility can include providing a superabsorbent material that includes a porous network structure formed from a mixture of a plurality of water soluble polysaccharides that are not chemically crosslinked together. The superabsorbent material can be administered to a subject in an effective amount to reduce glucose bioaccessibility in the subject. In some aspects, the treatment for reducing glucose bioaccessibility with the superabsorbent material retains a substantially unaltered fatty acid bioaccessibility. In some aspects, the treatment for reducing glucose bioaccessibility with the superabsorbent material retains a substantially unaltered protein bioaccessibility.

In some embodiments, a kit for reducing glucose bioaccessibility can include a superabsorbent material that includes a porous network structure formed from a mixture of a plurality of water soluble polysaccharides that are not chemically crosslinked together. The kit can also include instructions for a subject to consume the superabsorbent material in an effective amount to reduce glucose bioaccessibility in the subject.

In some embodiments, the superabsorbent material includes a porous network structure formed from a mixture of a plurality of water soluble polysaccharides that are not chemically crosslinked together. The plurality of water soluble polysaccharides includes at least two of agar, konjac gum, carrageenan, locust bean gum, xanthan gum, tamarind seed gum and guar gum carrageenan, alginate (such as sodium alginate), pectin, gellan gum, chitosan, Arabic gum, and a soluble starch. In some aspects, the plurality of water soluble polysaccharides includes at least two of agar, konjac gum, and carrageenan.

In some aspects, the superabsorbent material is administered in a dried and/or powdered form. In some aspects, the superabsorbent material is administered in a hydrated gel form. In some aspects, the superabsorbent material is administered in a hydrated liquid form.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 1 includes a graph of data that shows the cumulative bioaccessibility of total glucose from simulated in vitro jejunum and ileum with and without the superabsorbent material.

Figure 1:
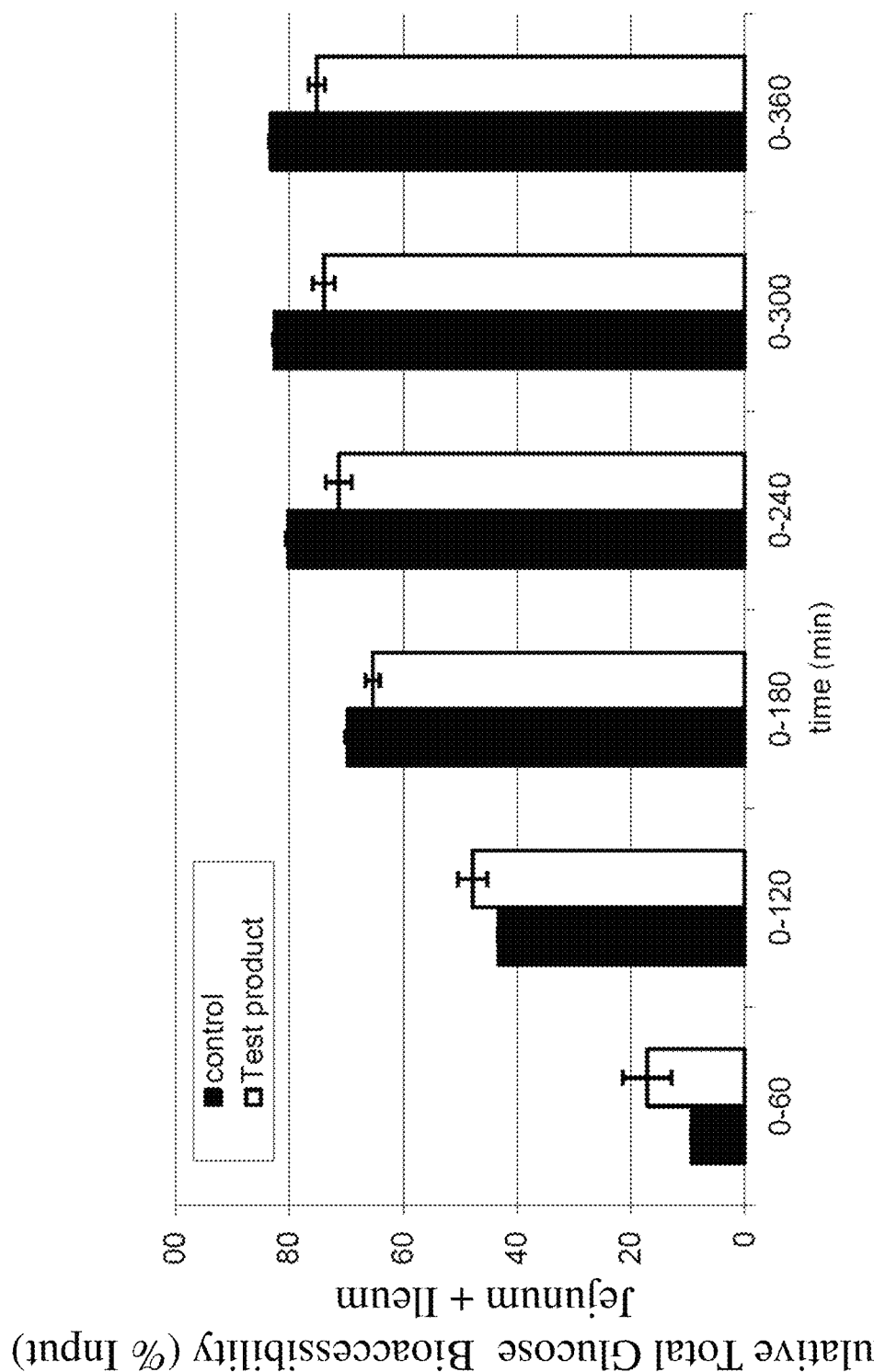

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present technology is directed to the fields of pharmaceutical science, nutritional science, and clinical medicine. Various embodiments relate generally to methods and compositions for the prevention, mitigation, or treatment of overconsumption of glucose and glucose-generating foods and the symptoms and biological effects thereof (e.g., obesity, diabetes, etc.).

Generally, the present technology is related to the treatment of reducing bioaccessibility of consumed glucose in a subject with a superabsorbent material. The superabsorbent material is administered in a way such that the consumed glucose or glucose generated from food has a lower bioaccessibility of glucose compared to when the glucose or glucose generating food is consumed without any superabsorbent material. The superabsorbent material is configured to have a significant volume of expansion once consumed and/or introduced into an aqueous environment. The superabsorbent material can be administered to a subject for the treatment of reducing glucose bioaccessibility in a variety of administration regimens and in a variety of dosage forms. The superabsorbent material can expand in the gastrointestinal tract of the subject in order to provide the treatment of reducing glucose bioaccessibility. The superabsorbent material may reduce, inhibit, prevent, treat or otherwise mitigate susceptibility, onset, development or progression in the disease state and symptoms associated with glucose or glucose generating food overconsumption that leads to high glucose bioaccessibility and bioavailability. In some instances, the treatment for reducing glucose bioaccessibility is for subjects that are obese or have diabetes.

In some embodiments, the treatment for reducing glucose bioaccessibility can be performed without significantly altering bioaccessibility of fatty acids. Accordingly, a subject consuming food and the superabsorbent material can have reduced glucose bioaccessibility while the bioaccessibility of fatty acids is not reduced. This can allow for a tailored approach to reducing the glucose available for absorption without reducing the availability of fatty acids for absorption from the consumed food. This approach can reduce the negative consequences of overconsuming glucose or carbohydrates without significantly altering the availability of fatty acids, which can be beneficial in a number of biological processes. Thus, the subject can still obtain the nutritive value of fatty acids without the negative consequence of overly bioaccessible glucose.

In some embodiments, the treatment for reducing glucose can be performed without significantly altering bioaccessibility of proteins. Accordingly, a subject consuming food and the superabsorbent material can have reduced glucose bioaccessibility while the bioaccessibility of proteins is not reduced. This call allow for a tailored approach to reducing the glucose available for absorption without reducing the availability of proteins for absorption from the consumed food. This approach can reduce the negative consequences of overconsuming glucose and carbohydrates without significantly altering the availability of consumed protein, which can be beneficial in a number of biological processes. Thus, the subject can still obtain the nutritive value of proteins without the negative consequence of over-absorbed glucose.

In some embodiments, the superabsorbent material is administered in an effective amount to reduce glucose bioaccessibility in the subject, wherein the subject is obese. For example, the reduction of glucose bioaccessibility can be used to help treat obesity in the subject by reducing the amount of glucose that can be absorbed. Accordingly, the treatments of the present technology that can be performed with administered superabsorbent material can be for obese subjects for the reduction of glucose bioaccessibility. Additionally, the prophylactic use of the superabsorbent material can be for subjects with a normal weight range; however, it is possible that a subject in the underweight range could desire a prophylactic against negative consequences of overconsumption of carbohydrates and thereby overabsorption of glucose, such as obesity and diabetes. Accordingly, the superabsorbent material can be provided as a treatment against developing a disease state associated with overconsumption of glucose for any subject, especially as a prophylactic. In some aspects, the superabsorbent material is provided in an effective amount as a prophylactic to inhibit progression of obesity or diabetes in the subject, wherein the subject is selected from: not obese; developing obesity; obese; or morbidly obese (e.g., extreme or severe obesity). While subjects are commonly humans, a subject may also be any animal that is capable of being obese, where mammals like mice, rats, cats, dogs, pigs, goats, cows, horses, or others may also be veterinary subjects.

In some embodiments, a treatment for reducing glucose bioaccessibility can include providing a superabsorbent material for use in the treatment. The superabsorbent material can include a porous network structure formed from a mixture of a plurality of water soluble polysaccharides that are not chemically crosslinked together. That is, the polysaccharides are not chemically attached to each other or linked together with any chemical linker. The polysaccharides are separate strands from each other. The polysaccharides are associated during a heating and freezing process to form a network of interconnected polysaccharides. The superabsorbent material can be administered to a subject in an effective amount to provide a treatment for reducing glucose bioaccessibility in the subject. The treatment for reducing glucose bioaccessibility can be determined by monitoring characteristics related to overconsumption of glucose and carbohydrates (e.g., obesity and diabetes), and identifying a reduction of characteristics associated with overconsumption of glucose or carbohydrates, or a reduction in rate of increase in such characteristics. As such, a subject that is obese may perform the treatment for reducing glucose bioaccessibility in order to reduce their obesity or diabetes. Also, a subject that may be developing obesity or diabetes or even worried about developing obesity or diabetes can perform the treatment by administration of the superabsorbent material as a prophylactic to reduce glucose bioaccessibility. The treatment of reducing glucose bioaccessibility can inhibit the onset or progression of obesity or diabetes in a subject when the superabsorbent material is administered to a pre-obese subject or pre-diabetic subject. A subject that is not obese or diabetic may also perform the treatment of reducing glucose bioaccessibility as a prophylactic measure in an attempt to stop onset of obesity or diabetes, or inhibit development of obesity or diabetes.

In another aspect, provided herein is a method of preventing or treating a disease or condition associated with glucose and carbohydrate overconsumption, such as from high carbohydrate caloric consumption. The method comprises orally administering to a subject suffering from or at an elevated risk of a disease or condition associated with glucose and carbohydrate overconsumption, such as from high caloric consumption, an effective amount of the superabsorbent material.

The treatment of reducing glucose bioaccessibility can include reducing glucose absorption by the gut of the subject. The reduction in absorption of glucose by the gut can be facilitated by the superabsorbent material absorbing glucose or otherwise modulating the environment so glucose is not readily absorbed, or some other mechanism of action. It is thought that the reduction of glucose bioaccessibility with the superabsorbent material may be correlated with reduced glucose absorption from the gut.

The treatment of glucose bioaccessibility can include absorbing glucose from the gut of the subject into the superabsorbent material. The superabsorbent material is absorbent, and thereby when in the digestive system can absorb substances, such as glucose. As such, the superabsorbent material may absorb substances that are then excreted out with the superabsorbent material.

The administration of the superabsorbent material together with a meal was studied to determine any changes to bioaccessibility of glucose, fatty acids, and proteins in the meal. The data shown in FIGS. 1-9 indicate that the superabsorbent material inhibits bioaccessibility of glucose without inhibiting the bioaccessibility of fatty acids and proteins. As such, the superabsorbent material appears to be selective in bioaccessibility modulation. The data showed lower total glucose bioaccessibility compared to experiments without test product. This effect was seen for the ileum compartment and could be observed between 60 min and 240 min of experiment. The administration of the superabsorbent material together with the meal resulted in similar total (jejunum+ileum) protein bioaccessibility compared to control. Most proteins became bioaccessible in the jejunum. For ileum, the nitrogen bioaccessibility was lower for experiments with superabsorbent material compared to control. The administration of the superabsorbent material together with the meal resulted in similar bioaccessibility of total fatty acids.

Another observation is that glucose and protein were more bioaccessible during the first 60 min in experiments with superabsorbent material. This could be explained by faster gastric emptying of the meal in experiments with superabsorbent material due to higher volume in the stomach compartment. The carbohydrate digestion happens quickly and hence could explain faster bioaccessibility of glucose with superabsorbent material which is not mixed well in the beginning. In conclusion, administration of the superabsorbent material to a meal resulted in lower glucose bioaccessibility, and similar protein and total fatty acid bioaccessibility.

In some embodiments, the treatment of reducing glucose bioaccessibility includes reducing weight of the subject. This can include administering the superabsorbent material in an amount effective to reduce glucose bioaccessibility and thereby reduce glucose absorption, which can lead to a reduction in the subject's weight. For example, the subject can have an initial weight prior to receiving the superabsorbent material, and subsequently during and/or after the treatment the subject can have a weight that is lower than the initial weight. The subject can weigh themselves during the treatment to track their weight to determine weight loss from an initial weight. The weight loss can also be tracked along sequential timepoints, which can provide a profile of weight loss for the subject.

In some embodiments, the treatment of reducing glucose bioavailability includes reducing the rate of weight gain in the subject. A subject may have a period of weight increase where they are trending toward obesity or more severe obesity at a higher weight. The subject can then perform the treatment for reducing glucose bioaccessibility with the superabsorbent material in order to slow down the rate of glucose absorption and thereby slow weight gain. For example, the subject may have a weight gain rate of 5 pounds every 2 months before the treatment, and then have a reduced weight gain rate of 4 or fewer pounds every 2 months. It is important to note that any reduction in rate of weight gain can be beneficial to a subject.

In some embodiments, the treatment of reducing glucose bioaccessibility includes promoting or otherwise increasing rate of weight loss in the subject. A subject may have a period where they are actively losing weight, whether with the superabsorbent material alone or with a change in lifestyle. For example, the subject may change from an unhealthy lifestyle (e.g., poor eating, high calorie, high fat foodstuffs, etc.) to eating healthy (e.g., portion control, low fat foods, low daily calorie consumption, etc.). The trend toward a healthy lifestyle may induce weight loss and decrease diabetic episodes. Additionally, the combined use of the superabsorbent material with an improved lifestyle may promote an increase in rate of weight loss and reduction of diabetic episodes.

In some embodiments, a treatment for reducing glucose bioaccessibility can include providing a superabsorbent material that includes a porous network structure formed from a mixture of a plurality of water soluble polysaccharides that are not chemically crosslinked together. The superabsorbent material can be administered to a subject in an effective amount to reduce glucose bioaccessibility in the subject. In some aspects, the treatment for reducing glucose bioaccessibility with the superabsorbent material retains a substantially unaltered fatty acid bioaccessibility. In some aspects, the treatment for reducing glucose bioaccessibility with the superabsorbent material retains a substantially unaltered protein bioaccessibility.

In some embodiments, the methods of reducing glucose bioaccessibility include providing the subject having consumed food, the food being a glucose-containing food or a glucose-generating food, and administering the superabsorbent material before, during or after the subject has consumed the food. The superabsorbent material can be administered in any format, such as a separate consumable or an additive to a meal or drink. The timing of administering the superabsorbent material can be from up to 60 minutes after consuming a meal or other foodstuffs, up to 45 minutes, up to 30 minutes, or up to 15 minutes prior to consuming a meal or other foodstuffs, or any range between any of these values. The timing of administering the superabsorbent material can be from up to 60 minutes, up to 45 minutes, up to 30 minutes, or up to 15 minutes after consuming a meal or other foodstuffs, or any range between any of these values. In some aspects, the glucose-generating food is a carbohydrate.

In some aspects, the administered superabsorbent material is from about 0.01% to about 20% by weight of the consumed food, from about 0.1% to about 15% by weight, from about 0.5% to about 10% by weight, from about 1% to about 8% by weight, or from about 2% to about 5% by weight, or any range between any of these values.

In some aspects, the administered superabsorbent material has an average particle size of from about 0.1 micron to 1 mm, from about 1 micron to 0.8 mm, from about 10 microns to about 0.6 mm, from about 0.1 mm to about 0.5 mm, or from about 0.3 mm to about 4 mm, or about 20-40 mesh.

In some aspects, the superabsorbent material is administered from about 0.1 g to about 20 g, from about 0.5 g to about 15 g, about 1 g to about 10 g, from about 2.5 g to about 7.5 g, or about 4 g per dose.

In some embodiments, the method results in bioaccessibility of total glucose being reduced with the superabsorbent material compared to total glucose bioaccessibility without the superabsorbent material. In some aspects, the bioaccessibility of total glucose is reduced with the superabsorbent material compared to total glucose bioaccessibility without the superabsorbent material after about 60 minutes after consumption of the food. In some aspects, bioaccessibility of total glucose is reduced with the superabsorbent material compared to total glucose bioaccessibility without the superabsorbent material before about 140 minutes after consumption of the food.

In some embodiments, the method can include administering the superabsorbent material in an effective amount to inhibit an increase or reduce at least one of: weight of the subject; total cholesterol in the subject; low-density lipoprotein (LDL) in the subject; high-density lipoprotein (HDL) in the subject; fasting insulin level in the subject; fasting leptin level in the subject; a HOMA-IR value for the subject; fat in the subject; or fatty liver disease in the subject.

In some embodiments, a kit for reducing glucose bioaccessibility can include a superabsorbent material that includes a porous network structure formed from a mixture of a plurality of water soluble polysaccharides that are not chemically crosslinked together. The kit can also include instructions for a subject to consume the superabsorbent material in an effective amount to reduce glucose bioaccessibility in the subject.

In some embodiments, the superabsorbent material includes a porous network structure formed from a mixture of a plurality of water soluble polysaccharides that are not chemically crosslinked together. The plurality of water soluble polysaccharides includes at least two of agar, konjac gum, carrageenan, locust bean gum, xanthan gum, tamarind seed gum and guar gum carrageenan, alginate (such as sodium alginate), pectin, gellan gum, chitosan, Arabic gum, and a soluble starch. In some aspects, the plurality of water soluble polysaccharides includes at least two of agar, konjac gum, and carrageenan. In some aspects, the superabsorbent material is administered in a dried and/or powdered form. In some aspects, the superabsorbent material is administered in a hydrated gel form. In some aspects, the superabsorbent material is administered in a hydrated liquid form.

Figure 10:
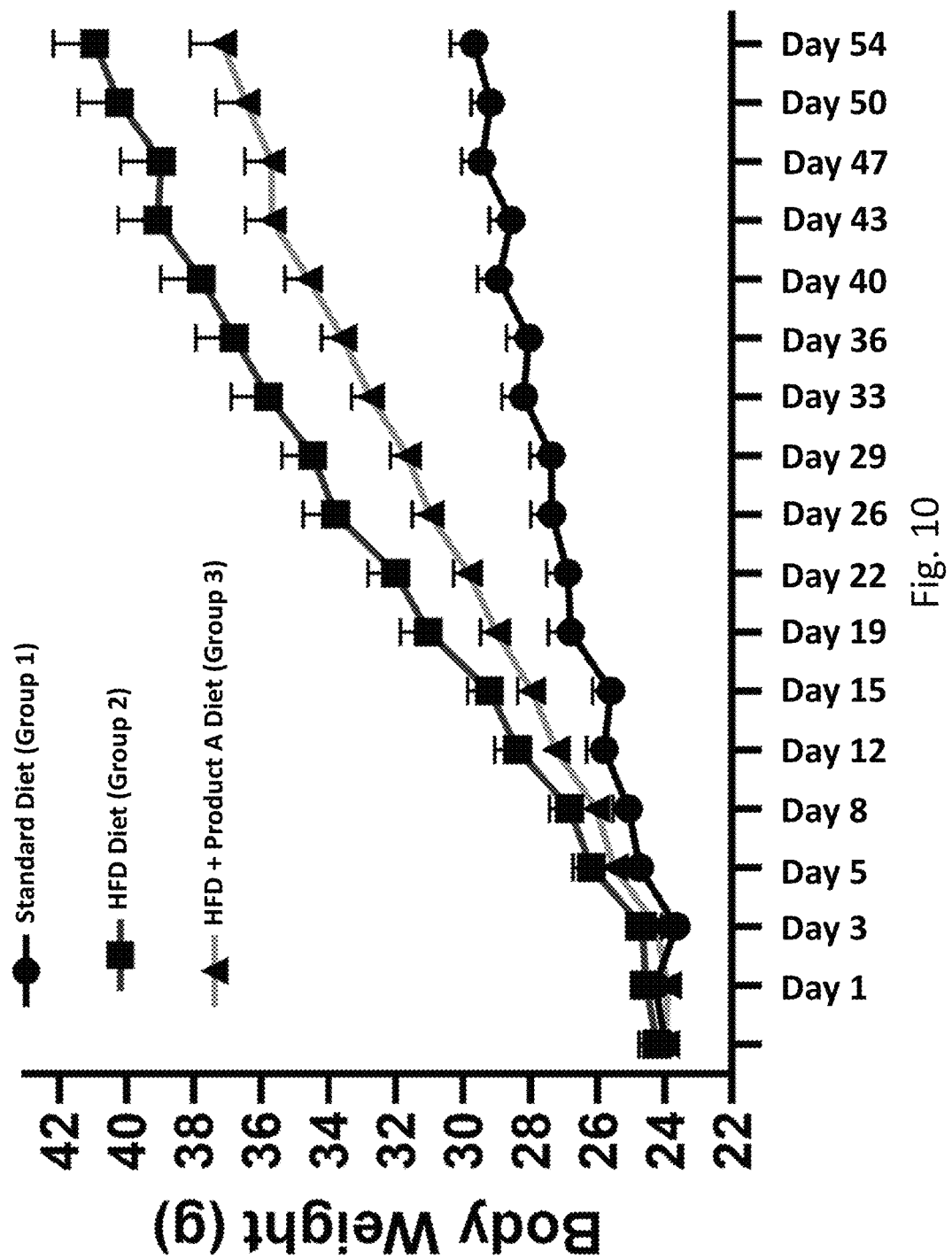
FIG. 10 includes a graph of data that shows the bodyweight in grams per day for the mice in the study, where the mice are in groups based on the diets: (Group 1) Standard Diet (e.g., standard rodent chew diet), (Group 2) High-fat Diet (HFD), and (Group 3) High-fat Diet-Treatment 1 (HFD+Product A, superabsorbent material).

In some embodiments, the treatment of reducing glucose bioaccessibility includes administering the superabsorbent material so that the subject has a slower rate of body weight gain. That is, the reduction of glucose bioaccessibility results in less glucose absorbed and reduces production of fat. The slower rate can be compared to the subject having a higher rate of body weight gain prior to being administered the superabsorbent material. The superabsorbent material has been shown to slow the rate of body weight gain, such as shown in data provided herein in FIG. 10. The reduction in the rate of weight gain was shown in the mice being treated with the superabsorbent material. The slower rate can be compared to the subject having a higher rate of body weight gain with a high glucose diet prior to being administered the superabsorbent material. In some aspects, the subject has a high glucose diet prior to being administered the superabsorbent material, and potentially during and after being administered the superabsorbent material. The reduction of body weight gain rate can be useful for treating diabetes due to the link with obesity.

The treatment of reducing glucose bioaccessibility can include administering the superabsorbent material in an effective amount to reduce a fasting insulin level in the subject. The fasting insulin level can be related to the high glucose diet in the subject. The fasting insulin level is related to insulin resistance, where insulin resistance is associated with higher fasting insulin levels compared to no insulin resistance. Higher fasting insulin levels can be from high glucose consumption and absorption. In part, the higher fasting insulin levels are related to insulin resistance in the obese person, which can be due to high glucose consumption. The superabsorbent material has been shown to reduce fasting insulin level, such as shown in the data provided herein in FIG. 11. Accordingly, administering the superabsorbent material in an effective amount has been shown to inhibit fasting insulin levels from increasing in the subject.

The treatment of reducing glucose bioaccessibility can include administering the superabsorbent material in an effective amount to reduce a fasting leptin level in the subject. Obese people, such as those that consume high levels of glucose have unusually high levels of leptin. This is because in some obese people, the brain does not respond to leptin, so they keep eating despite adequate (or excessive) fat stores, a concept known as 'leptin resistance'. This causes the fat cells to produce even more leptin. The fat cells may be a consequence of overconsumption of glucose. As such, measuring high leptin levels can indicate obesity, and low leptin levels can indicate no obesity or at least reduced obesity. The superabsorbent material has been shown to reduce fasting leptin levels, such as shown in the data provided herein in FIG. 12. Accordingly, administering the superabsorbent material in an effective amount has been shown to inhibit fasting leptin levels from increasing in the subject.

The treatment for reducing glucose bioaccessibility can include administering the superabsorbent material in an effective amount to reduce a HOMA-IR value for the subject. The homeostatic model assessment (HOMA) is a method used to quantify insulin resistance and beta-cell function in relation to glucose. The HOMA-IR equals (glucose×insulin)/22.5. Here, IR indicates insulin resistance, and the measurements are taken for fasting glucose and fasting insulin. The higher the HOMA-IR, the higher the glucose and insulin resistance, and lower the HOMA-IR, the lower the glucose and insulin resistance. As such, the HOMA-IR value can be used as a measurement of insulin resistance, especially because glucose levels and insulin levels are indications of insulin resistance. Accordingly, the blood glucose and insulin profiles were assessed at the end of the study under fasting conditions. The superabsorbent material has been shown to reduce the HOMA-IR value, such as shown in the data provided herein in FIG. 13. Accordingly, the administering the superabsorbent material in an effective amount has been shown to inhibit HOMA-IR value of the subject from increasing.

In some embodiments, the superabsorbent material includes a plurality of water soluble polysaccharides. The plurality of water soluble polysaccharides can include at least two of agar, konjac gum, carrageenan, locust bean gum, xanthan gum, tamarind seed gum and guar gum carrageenan, alginate (such as sodium alginate), pectin, gellan gum, chitosan, Arabic gum, and a soluble starch. In some aspects, the plurality of water soluble polysaccharides includes at least two of agar, konjac gum, and carrageenan, and all three in some instances. In some aspects, the superabsorbent material is administered in a dried and/or powdered form. In some aspects, the superabsorbent material is administered in a hydrated gel form or hydrated liquid form.

In some embodiments, a food composition can be used for delivering the superabsorbent material. The food composition can include any foodstuff, such as a high fat diet foodstuff, and a superabsorbent material in the foodstuff. The superabsorbent material can be configured as described herein and include a porous network structure formed from a mixture of a plurality of water soluble polysaccharides that are not chemically crosslinked together. The foodstuff can be any consumable composition that includes the superabsorbent material. Accordingly, a separate container of superabsorbent material can be provided and added to the food prior to consumption.

In some embodiments, a kit can be provided for the treatment of reducing glucose bioaccessibility. The kit can include a superabsorbent material in an administrable form. The administrable form includes the superabsorbent material with a porous network structure formed from a mixture of a plurality of water soluble polysaccharides that are not chemically crosslinked together. The kit also includes instructions for a subject to consume the superabsorbent material in an effective amount to reduce glucose bioaccessibility. For example, the instructions can include a dosing regimen for daily administration. The administration can be periodic, such as every period of time (e.g., every 4, 6, 8, 10, 12, or 24 hours), or discretionary, such as when taken prior to, during, or after a meal.

Superabsorbent Material

In some embodiments, the superabsorbent material is provided as a combination of polysaccharides (of natural origin or derived therefrom) formulated to have a significant volume expansion. The volume expansion may be induced by absorption of substances, such as body fluids. Aqueous environments can facilitate absorption and expansion by the superabsorbent material.

The superabsorbent material can include agar or carrageenan (e.g., at least 20% (wt %)), and optionally one or more water-soluble natural polysaccharides. In some embodiments, the water-soluble natural polysaccharide includes but is not limited to agar, konjac gum, carrageenan, locust bean gum, xanthan gum, tamarind seed gum and guar gum carrageenan, alginate (such as sodium alginate), pectin, gellan gum, chitosan, Arabic gum, and a soluble starch. The superabsorbent material has a superior swelling capacity (both in terms of water absorption ratio and volume expansion ratio) at room temperature (for example, at a temperature between 15° C. and 25° C.), or at human body temperature (for example, at a temperature between 35° C. and 41° C.), and/or under a neutral pH condition or a human gastric pH condition. In some embodiments, the superabsorbent material disclosed herein has a highly porous structure that is stable and reversible in the drying and rehydration processes under neutral and low pH solution mimicking human gastric condition. Upon rehydration, the superabsorbent material can expand in volume rapidly (in less than 25 minutes) and maintain a well-defined shape for at least 24 hours under a neutral pH condition or a human gastric pH condition. In some embodiments, the superabsorbent material disclosed herein is stable under an acidic pH such as a gastric pH and maintains the structure and the volume under the acidic gastric pH such that the induced satiety effect in a subject is prolonged.

A variety of water-soluble natural polysaccharides including agar, konjac gum, carrageenan, locust bean gum, xanthan gum, tamarind seed gum, guar gum, etc. are known to possess health benefits as dietary fiber with zero calories (undigestible to human enzymes). Attempts to use these dietary fiber materials to control calorie intake, obesity and other health problems have been made by extensive efforts. However, most of the applications involving the use of these natural polysaccharide materials either do not maintain a certain shape upon rehydration with water or gastric liquid or have poor water absorption and volume expanding capability. Therefore, in previous attempts of use they are cleared by the gastric system quickly and are not very effective in inducing satiety. Now, however, the water-soluble natural polysaccharides can be prepared with the heating and freezing protocol described herein to form a porous structure that is superabsorbent.

In one aspect, provided herein is a superabsorbent material comprising agar, carrageenan, a combination of agar and one or more water-soluble natural polysaccharides, or a combination of carrageenan and one or more water-soluble natural polysaccharides. In some embodiments, the one or more water-soluble natural polysaccharides include but are not limited to agar, konjac gum, carrageenan, locust bean gum, xanthan gum, tamarind seed gum and guar gum carrageenan, alginate (such as sodium alginate), pectin, gellan gum, chitosan, Arabic gum, and a soluble starch. The superabsorbent materials can be obtained by the process disclosed herein.

Disclosed herein are novel superabsorbent materials that are made from water-soluble natural polysaccharides with known health benefits and/or food application qualities (e.g., gelling strength, desirable texture, etc.), so the resulting composite natural polysaccharides have the desirable functionalities including but not limited to quick absorbance of a large amount of water upon rehydration with water or gastric liquid at room temperature (around 25° C.) or body temperature (around 37° C.), and quick swelling in volume and maintaining a certain shape and non-aggregated state in water or gastric liquid. The disclosed superabsorbent materials are effective in reducing glucose bioaccessibility and have great applications in weight control and preventing or treating other health problems such as obesity or diabetes.

The disclosed superabsorbent materials comprise an optimized combination of natural polysaccharides (composition ratio and total mass concentration). Upon subjecting to a series of physical treatments that induce and/or enhance the interactions between the natural polysaccharide molecules without using any chemical modifications or crosslinking and dehydration, the superabsorbent materials can form and maintain over a prolonged period of time a porous structure. Any dehydration protocol can be used as long as the drying process can maintain the gel matrix structural without diminishing the water absorption capacity and volume expansion function.

To obtain the disclosed superabsorbent materials, a variety of parameters were tested, including various combination of natural polysaccharides (composition ratio and total mass concentration), and various processing methods were carried out to produce a series of composite natural polysaccharides that have a range of water absorption and volume expanding properties, and shape maintaining (when in contracted or expanded state) properties (e.g., shape may change during expansion from contracted to expanded shape). These natural polysaccharide composite materials with different water absorption, volume expansion and shape stability (when in contracted or expanded state) can be used in a variety of applications. Some examples of the advantages of the disclosed superabsorbent materials and technology are summarized below. By being shape stable, the composition does not deform on its own or otherwise flow from normal gravity.

First, synergistic effects in solution and in the gelling process of certain natural polysaccharides can be achieved by the selection of the polysaccharides, the particular ratio range of the selected polysaccharides, and the mass concentration range of the materials. Second, the superabsorbent materials have superior properties in volume expansion and a well-defined shape upon rehydration due to their matrix structure providing enhanced stability and high swelling capacity with respect to absorbent ratio and volume expansion. Unlike conventional technology and materials, the disclosed technology and materials do not use modified or synthetic polymers or chemical crosslinking. As disclosed herein, the gel strength of the materials can be enhanced by freezing treatment of the gel. Finally, since the final product is in a dehydrated form that can be used to absorb water and expand volume to a certain shape upon rehydration, it is important to develop a process that can remove water from the composite gel while maintaining its structural integrity and functionality. Among the many possible dehydration methods that satisfy the aforementioned criteria, disclosed are a thawing-drying method and a freeze-drying method. By thawing-drying, the preformed gel is thawed and then dried at a temperature (e.g., 50-60° C.) without melting the gel structure under atmospheric pressure. By freeze-drying, the preformed frozen gel is directly lyophilized under vacuum. Both methods yield samples with good to great water absorption and volume expansion properties. In some embodiments, the freeze-dried samples have a more porous structure and higher water absorption capacity, while the thawing-dried samples have a more compact structure in the dry state but can resume a porous structure upon rehydration, although its water absorption capacity is lower than that of freeze-dried samples.

There are a wide range of high-quality water-soluble dietary fibers that are non-toxic to the human body, low in calories, and cannot be digested and decomposed by gastric acid and enzymes in the human body. These include seaweed polysaccharides, such as agar and carrageenan extracted from marine algae, konjac flour, guar gum, pectin, locust bean gum, tamarind polysaccharide gum, etc. extracted from plants, xanthan gum extracted by microorganism fermentation, and microbial polysaccharides such as gellan gum. The superabsorbent material prepared from these natural polysaccharides have the functions of promoting intestinal peristalsis, laxative, detoxification, and preventing intestinal diseases; slowing postprandial blood glucose rise (e.g., reducing glucose bioaccessibility) and reducing the risk of diabetes; lowering cholesterol and reducing the risk of cardiovascular and cerebrovascular diseases; and improving the metabolism of neutral fat and lipid and inhibiting body fat accumulation.

Agar is a water-soluble polysaccharide extracted from red algae. At room temperature, agar can absorb water and swell, but it needs to be heated to above 80° C. to dissolve in water. When the agar solution is cooled to 32-42° C., it will start to solidify into gel, and the solidified agar gel needs to be heated to 75° C. or above before it can melt again. Thus, agar is uniquely advantageous in many applications. In addition, compared with other natural gelling agents, agar has self-gelling property, that is, it does not require any additional substance during gelling process. Thus, agar gel is a purely natural product. Further, agar cannot be digested and absorbed by the human body, and therefore is widely used in food, biological applications, and medicine.

Carrageenan is another water-soluble polysaccharide extracted from red algae. Based on structural differences, carrageenans are divided into three main classes: Kappa, Iota, and Lambda. κ-carrageenan can swell in water at room temperature but can only dissolve in water at a temperature above 70° C. When the carrageenan solution is cooled to 20-25° C., it will start to solidify into gel (or it can form a gel at higher temperatures when KCl is added), and the solidified carrageenan gel needs to be heated to 47° C. or above before it can melt again.

Konjac gum (konjac glucomannan, KGM) is derived from Amorphophallus Konjac species, it is a high molecular polysaccharide made of residues of mannose and glucose, linked together by β-1,4 with a molar ratio of 1.6:1.0. It is a slightly branched polysaccharide having a molecular weight of 200,000 to 2,000,000 Daltons (the actual molecular weight of KGM depends on the konjac variety).

As described above, certain types of polysaccharide molecules can interact with each other in solution to generate synergistic effect in the gelling process. For example, in a mixed solution of agar that also contains carrageenan and konjac gum, when the temperature is increased to above 80° C., the agar molecules and the carrageenan/konjac gum molecules exist in the form of random coils. As the temperature of the solution decreases, the random coils of agar and possibly some carrageenan/konjac gum molecules start to interact with each other and form double helical structures; when the temperature is further reduced, the double helices will further interact with each other and self-assemble; and when the temperature drops to the gelling point, it can form a three-dimensional porous, network structure composed of agar molecules and carrageenan/konjac gum molecules. When the gel is further frozen for an extended period of time, any polysaccharide molecules, in particular carrageenan/konjac gum molecules, that are not incorporated in the gel matrix in the initial gelling step, may be induced to interact with the preformed agar gel network by the cryogelation effect. As a result, a composite material is formed with a highly stable porous structure that is capable of encapsulating a large amount of water molecules. By removing the water molecules while maintaining the three-dimensional porous, network structure, a superabsorbent material can be obtained.

In general, when a high temperature agar is mixed with one or more water-soluble natural polysaccharides, the agar molecules may interact with the other natural polysaccharide molecules as the temperature of the solution decreases. Due to the different molecular structures of the polysaccharides, the interactions between different natural polysaccharide molecules and the agar molecules are different. The resulting three-dimensional porous network structures and properties of the composite materials made from the agar and one or more water-soluble natural polysaccharide molecules are also different. By removing water molecules while maintaining the three-dimensional porous network structure formed by the agar molecules and the one or more natural polysaccharide molecules, a superabsorbent material can be obtained.

In some embodiments, the superabsorbent material comprises at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% (wt %) of agar and/or carrageenan, or any range between any of these values. In some embodiments, the superabsorbent material comprises at least 20% (wt %) of carrageenan. The agar or carrageenan and the one or more water-soluble natural polysaccharides do not form any chemical cross-linkage in the superabsorbent material but rather form strong molecular interactions induced by cryogelation or cryo-structuring to result in a highly porous network structure. The porous network structure is highly stable and reversible in the drying and rehydration processes in neutral and low pH solutions mimicking human gastric conditions.

The superabsorbent material has a great swelling capacity at room temperature (for example, at a temperature between 15° C. and 25° C.), or at human body temperature (for example, at a temperature between 35° C. and 41° C.), and under a neutral pH condition or a human gastric pH condition. Upon rehydration, the superabsorbent material can expand in volume rapidly in less than 2 hours, less than 1.5 hours, less than 1 hour, less than 30 minutes, or less than 15 minutes, (for example, in less than 25 minutes) and maintain a well-defined shape for at least 24 hours, at least 36 hours, or at least 48 hours under a neutral pH condition or a human gastric pH condition. In some embodiments, upon rehydration, the superabsorbent material can expand in volume rapidly in less than 25 minutes and maintain a well-defined shape for at least 24 hours under a neutral pH condition or a human gastric pH condition.

In some embodiments, the swelling capacity of the superabsorbent materials is measured by absorption ratio calculated by the formula: absorption ratio=(the weight of fully rehydrated sample)/(the weight of dry sample). For example, the superabsorbent material disclosed herein has an absorption ratio of at least 10 times or up to 200 times of its own weight in deionized water, or at least 5 times or up to 100 times of its own weight in artificial gastric juice. In some embodiments, the volume expansion capacity of the superabsorbent materials is measured by volume expansion ratio calculated by a formula: volume expansion ratio=(the volume of fully rehydrated sample)/(the volume of dry sample). For example, the superabsorbent material disclosed herein has a volume expansion ratio of at least 5 times and up to 150 times in deionized water or a volume expansion ratio of at least 5 times to up to 100 times in artificial gastric juice.

In some embodiments, the absorption ratio and/or the volume expansion ratio is measured at room temperature. In some embodiments, the absorption ratio and/or the volume expansion ratio is measured at about 37° C. In some embodiments, the absorption ratio and/or the volume expansion ratio is measured at a neutral pH. In some embodiments, the absorption ratio and/or the volume expansion ratio is measured at a physiological pH. In some embodiments, the absorption ratio and/or the volume expansion ratio is measured at a gastric pH. In some embodiments, the superabsorbent materials obtained by the process disclosed herein have a water absorption ratio of at least 10 fold, at least 20 fold, at least 30 fold, at least 40 fold, at least 50 fold, at least 60 fold, at least 70 fold, at least 80 fold, at least 90 fold, at least 100 fold, at least 110 fold, at least 120 fold, at least 130 fold, at least 140 fold, at least 150 fold, at least 160 fold, at least 170 fold, at least 180 fold, at least 190 fold, or at least 200 fold of the weight of the dry superabsorbent material before swelling, or within any range between any of these values. In some embodiments, the superabsorbent materials obtained by the process disclosed herein have a gastric fluid absorption ratio of at least 5 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, or at least 100 fold of the weight of the dry superabsorbent material before swelling, or within any range between any of these values. In some embodiments, the superabsorbent materials obtained by the process disclosed herein have a volume expansion ratio in water of at least 10 fold, at least 20 fold, at least 30 fold, at least 40 fold, at least 50 fold, at least 60 fold, at least 70 fold, at least 80 fold, at least 90 fold, at least 100 fold, at least 110 fold, at least 120 fold, at least 130 fold, at least 140 fold, or at least 150 fold of the weight of the dry superabsorbent material before swelling, or within any range between any of these values. In some embodiments, the superabsorbent materials obtained by the process disclosed herein have a volume expansion ratio in gastric fluid of at least 5 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, or at least 100 fold of the weight of the dry superabsorbent material before swelling, or within any range between any of these values.

Disclosed herein is a process of obtaining a superabsorbent material comprising the steps of combining agar and one or more water-soluble natural polysaccharides at various ratio and mass concentrations, heating the mixture in water to completely dissolve the agar and one or more water-soluble natural polysaccharides, and forming a gel by cooling the mixture, and further stabilizing the gel by cryogelation below freezing point. The obtained superabsorbent materials have a highly porous structure and can absorb a large number of water molecules. Upon dehydration at room or body temperature while maintaining the three-dimensional network structures, the obtained superabsorbent materials can absorb a large amount of water, expand in volume and maintain a well-defined shape at room or body temperature, and under neutral or gastric conditions. Unlike the unprocessed water-soluble natural polysaccharides, which are easily degradable in stomach, the superabsorbent materials disclosed herein can maintain its three-dimensional network structure for a prolonged period even in the gastric environment at human body temperature. In other words, the superabsorbent materials disclosed herein require higher than the gastric environment temperature (about 37° C.) to be re-dissolved in aqueous solution, thereby effectively overcoming the problem of quick metabolism and dissociation of water-soluble polysaccharides in gastric fluid when used to achieve weight loss. The superabsorbent materials disclosed herein have superior swelling capacity and water retention properties under physiological conditions in gastric fluid, allowing them wide application as dietary materials and/or delivery vehicles.

In yet another aspect, provided herein is a method of preparing a superabsorbent material comprising agar, carrageenan, a combination of agar and one or more water-soluble natural polysaccharides, a combination of carrageenan and one or more water-soluble natural polysaccharides, or a combination of agar and carrageenan and one or more water-soluble natural polysaccharides. The method comprises the steps of adding agar, carrageenan, a combination of agar and one or more water-soluble natural polysaccharide, a combination of carrageenan and one or more water-soluble natural polysaccharides, or a combination of agar and carrageenan and one or more water-soluble natural polysaccharides to water to form a mixture, heating the mixture to a temperature of between 80° C. and 100° C. with stirring until the one or more polysaccharides are completely dissolved, allowing the mixture to cool down to between 20° C. and 45° C. to form a gel over a period of 2 to 10 hours, freezing the preformed gel at a temperature below freezing temperature for at least 4 hours, and drying the frozen gel to obtain the superabsorbent material. In some embodiments, the drying step comprises thawing the gel and drying under normal pressure at 50-60° C. ("thawing-dry"). In some embodiments, the drying step comprises directly drying the frozen gel by lyophilization without thawing ("freeze-dry"). In some embodiments, the method further comprises pulverizing the dried gel to obtain the superabsorbent material in a powder form of various mesh sizes.

In another aspect, disclosed herein is a method of preparing a superabsorbent material comprising a combination of agar and one or more water-soluble natural polysaccharides. The method comprises the steps of: adding agar and one or more water-soluble natural polysaccharide, to water to form a mixture, heating the mixture to a temperature of between 80° C. and 100° C. with stirring until the one or more polysaccharides are completely dissolved, allowing the mixture to cool down to between 20° C. and 45° C. to form a gel over a period of 2 to 10 hours (the temperature and time for the gelling step can be optimized depending on materials used), freezing the preformed gel at a temperature below freezing for at least 4 hours (the temperature and time for the cryogelation step can be optimized depending on materials used), and drying the frozen gel to obtain the superabsorbent material by thawing the gel and drying under normal pressure at 50-60° C. (referred to as thawing-dry), or dry the frozen gel by lyophilization (referred to as freeze-dry), or any drying methods that can remove water without damaging the gel matrix structure and diminishing the water absorption capacity and volume expansion function. In some embodiments, the method further comprises pulverizing the dried gel to obtain the superabsorbent material in a powder form of various mesh sizes depending on specific application needs. In some embodiments, the drying step includes freeze-drying or vacuum freeze-drying the frozen gel. In some embodiments, the drying step includes thawing the frozen gel, filtering the thawed gel to obtain a filter cake, and drying the filter cake. The filter cake can be dried by any suitable method, including but not limited to air drying, heat drying, freeze-drying, vacuum drying, or a combination thereof.

The dried gel of any embodiment of superabsorbent material can be further pulverized into a powder form for easy storage and applications. As described herein, during the cooling process the agar and/or carrageen, and one or more natural polysaccharides can form a three-dimensional structure. In some embodiments, a three-dimensional, porous structure is formed as shown by SEM images. After dehydration and swelling, the shape and form of this three-dimensional structure can be maintained. As demonstrated in the working examples, the swelled superabsorbent materials appeared in a non-flowing gel state with a well-defined shape. Thus, the superabsorbent materials obtained by the disclosed process have superior swelling capacity in terms of volume expansion and shape stability and water retention properties.

As demonstrated in the working examples, different samples of the superabsorbent materials showed a wide range of water absorption capacity, suggesting that the composition, molar ratio, and concentration can affect the properties of the superabsorbent materials. The disclosed superabsorbent materials are characterized by highly stable and uniform structure, suggesting that molecules of different natural polysaccharides interact with each other to form a new and unique matter, rather than simple physical mixtures of various polymers which would be expected to show heterogeneous structural features. The different composite natural polysaccharide materials made from different compositions, ratio and concentration clearly have different structures, which explain their different functionalities such as water absorption ratio and volume expansion ratio and shape stability. The liquid nitrogen flash freezing followed by lyophilization captured the porous structural features of various composite natural polysaccharides materials.

In a related aspect, provided herein is a superabsorbent material produced by the method described above. The superabsorbent material produced by the disclosed method can be used in the food or health supplement industry and/or as delivery vehicle for therapeutic agents and/or nutrients.

The superabsorbent materials disclosed herein have various applications in healthcare and food industries. For example, the superabsorbent material can be used as a medical diet or dietary supplement, which can reduce glucose bioaccessibility. Such a diet or dietary supplement, when used in combination with a therapy, can enhance the therapeutic effect on obesity and diabetes; and even when used alone, can prevent or delay the onset of certain diseases such as obesity and diabetes. In some embodiments, the superabsorbent materials disclosed herein can be used as a vehicle for loading medicine for the preparation of medical materials.

Some examples of the applications of the superabsorbent materials disclosed herein include but are not limited to the following: (1) the superabsorbent materials disclosed herein can be added to a cold or warm liquid diet or a drink such as water, juice, milk, beverage, soup, or pudding for human consumption; (2) the superabsorbent materials disclosed herein can be directly consumed in the form of a powder, a tablet, a capsule or any other suitable form, followed by drinking an appropriate amount of liquid to allow liquid absorption and swelling in the stomach; (3) the superabsorbent materials disclosed herein can be added as an ingredient to various food products such as bread, cakes, biscuits, energy bars and other foods to make low-calorie, dietary fiber-rich functional foods and/or a volumetrics diet to induce satiety for a prolonged time. Because the superabsorbent materials disclosed herein can be in dry powder form and has superior swelling capacity, a small amount of consumption (about 5 g to 20 g) can achieve a therapeutic effect. The superabsorbent materials are also stable under normal shipping and storage conditions. Therefore, the superabsorbent materials can also be used as a vehicle to deliver drugs and other nutrients.

In some embodiments, the superabsorbent material can be administered in a dosage in a range from 0.25 g to 750 g, from 0.5 g to 500 g, from 1 g to 100 g, from 10 g, to 90 g, from 20 g to 80 g, 30 g to 70 g, 40 g to 60 g, or some value therebetween. Low dose superabsorbent material can be considered to be from 0.24 g to 25 g, or 0.5 g to 20 g, from 1 g to 15 g, 5 g to 12 g, 6 g to 10 g, or about 8-9 g per dosage. The dosing can be once, twice, or three times daily, such as with meals.

In another aspect, provided herein is a dietary composition comprising the superabsorbent material described above. In another aspect, provided herein is a volumetrics diet comprising the superabsorbent material or the dietary composition disclosed herein.

In some embodiments, the superabsorbent material or the dietary composition comprising the superabsorbent material further comprises one or more additional essential nutrients including macronutrients and micronutrients. Such nutrients include but are not limited to a variety of proteins and active peptides, vitamins and trace elements and minerals, and prebiotics.

In some embodiments, the superabsorbent material has a volume expansion ration of at least 5 times or up to 150 times in deionized water. In some embodiments, the superabsorbent material is neither expanded with gas nor digested with an enzyme prior to or during formation of the superabsorbent material.

SUPERABSORBENT MATERIAL EXAMPLES

The observations described in Examples 1-23 can be reviewed in U.S. No. 2020/0197904, which is incorporated herein by specific reference in its entirety.

Example 1: Materials and Methods

Preparation of artificial gastric juice (according to the United States Pharmacopoeia): 2.0 g sodium chloride, 3.2 g pepsin (1500 U/mg), and 7.0 mL of concentrated hydrochloric acid were added to distilled water and the volume was adjusted to 1000 mL.

Absorption ratio test: 1.0 g of a dry superabsorbent material was mixed with 250 g of distilled water in a beaker, and the mixture was allowed to stand for 3 hours at 25° C. Then the sample in the beaker was poured onto a 120-mesh sieve and kept for 1 hour at 25° C. to allow the water to drip off naturally. The wet sample remaining on the sieve was recovered and weighed. The absorption ratio was calculated as follows: absorption ratio=(the weight of the wet sample recovered from the sieve)/(the weight of the starting dry sample).

Similarly, the absorption ratio of a sample superabsorbent material in the artificial gastric juice was tested using the procedure described above. Instead of the distilled water, 1.0 g of the dry sample was mixed with the artificial gastric juice and allowed to stand for 3 hours at 37° C. Then the wet sample was recovered and weighed, and the absorption ratio was calculated as described above.

Gel strength test: 1.5 g of agar was added to 98.5 g of deionized water. The mixture was stirred and heated to 90° C. until the agar was completely dissolved, then cooled to 20° C. to form an agar gel. The gel was allowed to stand for 24 hours before use. 1.5 g of κ-carrageenan was added to 98.3 grams of deionized water. The mixture was stirred and heated to 90° C. until κ-carrageenan was completely dissolved. 0.2 g of potassium chloride was added and then cooled to 20° C. to form a carrageenan gel. The gel was allowed to stand for 24 hours before use. The prepared agar gel and the carrageenan gel were tested for gel strength using a texture analyzer (Stable Micro Systems, TA.XT. Plus Texture Analyser, UK). The test settings were: probe P/0.5, pressing speed 1.5 mm/s, running speed 1.0 mm/s, recovering speed 1.5 mm/s, and the pressing distance was 20 mm. The agar gel and the carrageenan gel used herein had a measured gel strength of 1000 $g/cm^2$ and 1200 $g/cm^2$, respectively.

Viscosity test: 2.0 g of a water-soluble natural polysaccharide was added to 198 g of deionized water. The mixture was stirred at room temperature until the polysaccharide was completely dissolved. The viscosity of the solution was measured at 25° C. using a Brookfield viscometer. The measured viscosity of the starting materials used herein is listed in Table 1 below.

TABLE 1

Viscosity of Starting Materials

| Polysaccharide | Viscosity |
| --- | --- |
| Konjac gum powder aqueous solution | 22000 mpa·s |
| Locust bean gum aqueous solution | 2500 mpa·s |
| Guar gum aqueous solution | 3500 mpa·s |
| Xanthan gum aqueous solution | 3200 mpa·s |
| Tamarind seed gum aqueous solution | 60 mpa·s |

Examples 2-17

The characteristics of all samples from Examples 2-17 are summarized in Table 2 below. These examples were prepared as described with the ingredients and ratios of materials in the preparation condition. The preparation condition included heated mixing, such as temperatures to about 95° C. with stirring until the polysaccharides were completely dissolved, then slowly cooled to form a gel. The gel was kept at 10° C. for 2 hours, and then frozen for 10 hours in a −20° C. freezer to obtain a frozen gel. In some of the examples, direct freeze drying was used with to decrease the water content to 15-18% and pulverizing. In some examples, the frozen gel was thawed and filtered, and the filter cake was dried at 50° C. under the normal pressure to decrease the water content to 15-18% and then pulverized.

TABLE 2

Characterization of the Superabsorbent Materials

| Ex. No. | Samp. No. | Ingredients and ratio | Preparation Condition | Abs. ratio in water | Abs. ratio in gastric juice |
| --- | --- | --- | --- | --- | --- |
| 2 | 1 | Agar:κ-carrageenan: konjac gum = 1:1:1 | Simple mixture | 4.0 | 2.6 |
| 3 | 2 | Agar:κ-carrageenan: konjac gum = 1:1:1 Dry powder; Non-flowing hydrated gel state. | Superabsorbent material obtained by heated mixing to dissolve, slowly cooled to gel, then frozen for direct freeze drying. | 88.6 | 31.5 |
| 3 | 3 | Agar:κ-carrageenan: konjac gum = 1:1:1 Dry powder; Non-flowing hydrated gel state. | Superabsorbent material obtained by heated mixing to dissolve, slowly cooled to gel, then frozen, then thawed and dried at 50° C. then pulverized. | 97.2 | 34.5 |
| 4 | 4 | Agar:κ-carrageenan: konjac gum = 1:1:2 Dry powder; Non-flowing hydrated gel state. | Superabsorbent material obtained by heated mixing to dissolve, slowly cooled to gel, then frozen for direct freeze drying. | 79.7 | 29.5 |
| 4 | 5 | Agar:κ-carrageenan: konjac gum = 1:1:2 Dry powder; Non-flowing hydrated gel state. | Superabsorbent material obtained by heated mixing to dissolve, slowly cooled to gel, then frozen, then thawed and dried at 50° C. then pulverized. | 95.3 | 34.1 |
| 5 | 6 | Agar:κ-carrageenan: konjac gum = 2:1:1 Dry powder; Non-flowing hydrated gel state. | Superabsorbent material obtained by heated mixing to dissolve, slowly cooled to gel, then frozen for direct freeze drying. | 67.4 | 23.8 |
| 5 | 7 | Agar:κ-carrageenan: konjac gum = 2:1:1 Dry powder; Non-flowing hydrated gel state. | Superabsorbent material obtained by heated mixing to dissolve, slowly cooled to gel, then frozen, then thawed and dried at 50° C. then pulverized. | 68.9 | 26.0 |
| 6 | 8 | Agar:κ-carrageenan: konjac gum = 1:2:1 Dry powder; Non-flowing hydrated gel state. | Superabsorbent material obtained by heated mixing to dissolve, slowly cooled to gel, then frozen for direct freeze drying. | 105.4 | 23.7 |
| 6 | 9 | Agar:κ-carrageenan: konjac gum = 1:2:1 Dry powder; Non-flowing hydrated gel state. | Superabsorbent material obtained by heated mixing to dissolve, slowly cooled to gel, then frozen, then thawed and dried at 50° C. then pulverized. | 121.0 | 27.6 |
| 7 | 10 | Agar:κ-carrageenan: konjac gum = 1:2:1 Dry powder; Non-flowing hydrated gel state. | Superabsorbent material obtained by heated mixing to dissolve, slowly cooled to gel, then frozen for direct freeze drying. | 165.1 | 21.8 |
| 7 | 11 | Agar:κ-carrageenan: konjac gum = 1:2:1 Dry powder; Non-flowing hydrated gel state. | Superabsorbent material obtained by heated mixing to dissolve, slowly cooled to gel, then frozen, then thawed and dried at 50° C. then pulverized. | 195.0 | 26.5 |

TABLE 2-continued

Characterization of the Superabsorbent Materials

| Ex. No. | Samp. No. | Ingredients and ratio | Preparation Condition | Abs. ratio in water | Abs. ratio in gastric juice |
|---|---|---|---|---|---|
| 8 | 12 | Agar:κ-carrageenan: konjac gum = 1:2:1 Dry powder; Non-flowing hydrated gel state. | Superabsorbent material obtained by heated mixing to dissolve, slowly cooled to gel, then frozen, then thawed and dried at 50° C. then pulverized. | 73.2 | 36.0 |
| 9 | 13 | Agar:κ-carrageenan: konjac gum = 1:2:1 Dry powder; Non-flowing hydrated gel state. | Superabsorbent material obtained by heated mixing to dissolve, slowly cooled to gel, then frozen, then thawed and dried at 50° C. then pulverized. | 69.0 | 26.0 |
| 10 | 14 | Agar:κ-carrageenan: locust bean gum = 2:1:1 Dry powder; Non-flowing hydrated gel state. | Superabsorbent material obtained by heated mixing to dissolve, slowly cooled to gel, then frozen, then thawed and dried at 50° C. then pulverized. | 52.0 | 23.8 |
| 11 | 15 | Agar:κ-carrageenan: konjac gum:xanthan gum = 5:5:2:3 Dry powder; Non-flowing hydrated gel state. | Superabsorbent material obtained by heated mixing to dissolve, slowly cooled to gel, then frozen, then thawed and dried at 50° C. then pulverized. | 78.0 | 27.5 |
| 12 | 16 | Agar:κ-carrageenan: tamarind seed gum = 2:2:1 Dry powder; Non-flowing hydrated gel state. | Superabsorbent material obtained by heated mixing to dissolve, slowly cooled to gel, then frozen, then thawed and dried at 50° C. then pulverized. | 48.0 | 20.5 |
| 13 | 17 | Agar:κ-carrageenan: guar gum = 2:2:1 Dry powder; Non-flowing hydrated gel state. | Superabsorbent material obtained by heated mixing to dissolve, slowly cooled to gel, then frozen for direct freeze drying. | 57.0 | 21.8 |
| 14 | 18 | Agar only Dry powder; Non-flowing hydrated gel state. dried at 50° C. | Superabsorbent material obtained by heated mixing to dissolve, slowly cooled to gel, then frozen, then thawed and then pulverized. | 68.0 | 18.5 |
| 15 | 19 | κ-carrageenan only Dry powder; Non-flowing hydrated gel state. | Superabsorbent material obtained by heated mixing to dissolve, slowly cooled to gel, then frozen for direct freeze drying. | 32.7 | 15.6 |
| 16 | 20 | Agar:konjac gum = 1:1 Dry powder; Non-flowing hydrated gel state. | Superabsorbent material obtained by heated mixing to dissolve, slowly cooled to gel, then frozen, then thawed and dried at 50° C. then pulverized. | 36.0 | 20.5 |
| 17 | 21 | κ-carrageenan: konjac gum = 1:1 Dry powder; Non-flowing hydrated gel state. | Superabsorbent material obtained by heated mixing to dissolve, slowly cooled to gel, then frozen for direct freeze drying. | 27.0 | 17.8 |

Example 18

Additional examples of the preparation and characterization of additional samples of the superabsorbent materials are shown in Table 3 below.

TABLE 3

Characterization of Additional Samples of Superabsorbent Materials

| Sample No. | Ingredients and ratio | Concentration | Thawing/drying at 50-60° C. | | Freeze-dry | |
|---|---|---|---|---|---|---|
| | | | water absorption ratio (pH7) | water absorption ratio (pH1) | water absorption ratio (pH7) | water absorption ratio (pH1) |
| 22 | agar | 1.20% | 11.9 | 9.2 | 30.2 | 22.4 |
| 23 | agar + konjac gum (1:1) | 0.6% + 0.6% | 18.4 | 19.3 | 43.7 | 41.0 |
| 24 | agar + konjac gum + carrageenan (10:1:1) | 1.0% + 0.1% + 0.1% | 13.1 | 12.0 | 33.2 | 27.9 |
| 25 | agar + konjac gum + carrageenan (2:1:1) | 0.6% + 0.3% + 0.3% | 31.3 | 21.5 | 56.9 | 37.8 |
| 26 | agar + konjac gum + carrageenan (1:1:1) | 0.4% + 0.4% + 0.4% | 58.8 | 36.1 | 66.9 | 48.8 |
| 27 | agar + konjac gum + carrageenan (2:5:5) | 0.2% + 0.5% + 0.5% | 67.6 | 46.4 | 89.2 | 58.8 |
| 28 | agar + konjac gum + xanthan gum (1:1:1) | 0.3% + 0.3% + 0.3% | 58.9 | 28.3 | n/a | n/a |
| 29 | agar + locust bean gum + carrageenan (1:1:1) | 0.4% + 0.4% + 0.4% | 34.2 | 24.0 | n/a | n/a |
| 30 | agar + locust bean gum + xanthan gum (1:1:1) | 0.3% + 0.3% + 0.3% | 44.9 | 20.3 | n/a | n/a |
| 31 | agar + konjac gum + xanthan gum (3:1:1) | 0.6% + 0.2% + 0.2% | 37.7 | 18.7 | n/a | n/a |
| 32 | agar + locust bean gum + carrageenan (3:1:1) | 0.6% + 0.2% + 0.2% | 20.3 | 16.1 | n/a | n/a |

This batch of the samples were prepared by weighing each ingredient and being added to deionized water at the ratio and mass concentration as indicated in Table 3 and heating to 100° C. and stirring until all ingredients are fully dissolved. Each solution was cooled to 20° C. and stored in a 20° C. incubator for 6 hours, to form a stable gel. After 6 hours, the samples were transferred to a −20° C. freezer to store for 10 hours, thereby to obtain a cryo-stabilized gel. After 10 hours, the cryo-stabilized gel was thawed at room temperature, excess water was filtered off, and the sample was further air dried in a 50° C. incubator. Alternatively, after 10 hours of cryogelation at −20° C., the sample was lyophilized to dry where the gel was pre-frozen until its center reached −40° C., and the sample was kept below −10° C. throughout the lyophilization process until the sample was dry. The dried sample was pulverized to 20 mesh to obtain the powdered superabsorbent materials. The absorption ratio at different pH conditions was measured as described above.

As shown in Table 3, freeze-drying generally led to a higher water absorption ratio than thawing dry. Since the drying process was after the gel formation (20° C. for 6 hours) and stabilization by cryogelation (−20° C. for 10 hours), it is unlikely that the freezing methods will produce different structures. However, during thawing dry process, it is likely that the water was melted and some of the pores were collapsed. While most of the pores can be reformed upon rehydration, a fraction of pores may not be re-established, presumably because some of the surfaces that form the wall of the pore become associated with each other so strongly that they cannot be separated upon rehydration. By contrast, during the freeze dry process, the water remained in its solid form and removed by sublimation, so the pore structure may be better maintained. The types of materials also contributed to different properties of the superabsorbent materials. As shown in Table 3, Sample Nos. 22-25 demonstrated significantly different properties in the samples prepared by two different drying methods, suggesting their pore structures are more sensitive to the drying methods, whereas Sample Nos. 26 and 27 are less sensitive.

Example 19

This example demonstrates the volume expansion and shape stability of Sample Nos. 22-32. Sample Nos. 22-32 were soaked in deionized water for 24 hours, and images of a particle of each sample were taken before and after rehydration using a Leica light microscope (model MZ125). Sample No. 22 showed low volume expansion but had a well-defined shape. Sample No. 23 showed low to modest volume expansion and had a well-defined shape. Sample No. 24 showed a sheet-like expansion, appeared to be an inter-connected bundle of fibers but did not have a well-defined gel matrix shape. Sample No. 25 showed low-to-modest volume expansion and the shape appeared to be stacked sheets. Sample No. 26 showed high volume expansion but appeared to have an inter-connected, heterogeneous sheet structures. Sample No. 27 showed large volume expansion. After fully swollen, Sample No. 27 had a well-defined shape that appeared to have a homogeneous gel matrix structure. Sample No. 28 showed high volume expansion but appeared to have an inter-connected, heterogeneous sheet structures. Sample No. 29 showed good volume expansion and good shape structure as a well-defined homogeneous gel matrix structure. Sample Nos. 30 and 31 were similar to Sample No. 29 and showed good volume expansion and good shape structure as a well-defined homogeneous gel matrix structure. Sample No. 32 was similar to Sample No. 24 and showed a sheet-like expansion, appeared to be an inter-connected bundle of fibers but did not have a well-defined gel matrix shape. Thus, various samples expanded in volume upon rehydration, and the degree of volume expansion generally correlated with the water absorption ratio measured by weight. However, not all samples had a well-defined shape upon rehydration. For examples, Sample Nos. 24, 28, and 33, and to a lesser degree also Sample No. 26, had a looser structure in the rehydrated form. By contrast, Sample No. 27 had the best maintained shape.

Example 20

This example demonstrates the water absorption ratio and volume expansion kinetics of Sample No. 27. Kinetic analysis of water absorption and volume expansion was performed on Sample No. 27. A dry particle of Sample No. 27 was swelled in deionized water (pH7) and the length of the particle was measured at various time points. The kinetic analysis showed that the sample particle underwent volume expansion rapidly upon rehydration, more than doubling its size in less than 6 minutes, expanding volume by 16-fold in 19 minutes, and eventually reaching a volume that was approximately 120-fold of the original volume of the dry particle. Most of the expansion was completed within 100 minutes (reaching 90% of the maximally expanded volume).

Example 21

This example demonstrates the scanning electron microscopic imaging (SEM) analysis of various samples. Sample Nos. 22-32 from thawing-dry preparation were Sputter coater coated with Pt and imaged on a JOEL JSM-7001 Scanning electron microscope. SEM images for Sample Nos. 22, 23, 24, and 27 were obtained from thawing dry. Although different samples showed various surface features, it was hard to determine if such features were intrinsic to a given composite natural polysaccharide material, because the particle surface may be affected by the pulverization processes. Sample No. 27, and to a lesser degree also Sample No. 24, showed some parallelly organized surface structure as compared to the other two samples. However, the correlation to the functionalities such as water absorption and volume expansion of this observation is unclear. In general, the samples prepared by thawing-dry did not show any porous structures. However, by water absorption ratio measurement and volume expansion, these samples showed substantial ability to absorb water and expand in volume upon rehydration, suggesting that the matrix structure of the composite polysaccharide material is largely preserved in the thawing-dry process and can be fully or substantially established upon rehydration.

Example 22

This example demonstrates the scanning electron microscopic imaging (SEM) analysis of hydrated samples prepared by flash freezing and freeze-drying at different pH conditions: at pH 7 and at pH 1, respectively. To capture the structural features in the hydrated state, thawing-dried samples from Table 3 were soaked in deionized water (pH=7 or pH=1) for at least 12 hours, flash frozen in liquid nitrogen, and lyophilized to dry, sputter coated with platinum and imaged on a JOEL JSM-7001 Scanning electron microscope. For each sample, a number of particles were imaged. At pH 7, Sample No. 22 had a relatively dense structure, and may include some layered structural feature at the surface, which could be responsible for a certain level of water absorption observed with this sample. Sample No. 23 showed a cross-layered pore structure on one face and a fibrous pore structure on the other face. Although some samples had a puffy appearance, the pore size seemed to be very small. Sample No. 24 showed a parallel-layered structure. The zoomed-in view showed that each layer contains a network of small pores. Sample No. 25 showed a parallel-layered structure. The zoomed-in view shows that each layer contained a network of pores that were approximately 1-5 μm wide, and 5-10 μm long; these pores were interconnected and intertwined with each other. Sample No. 26 showed a very porous structure, but the pore structural pattern was less well-defined. Its surface did show a pattern of cross-layered pores. Sample No. 27 showed a characteristic parallel-layered large pore (10-20 μm wide, and 100-200 μm long) that seemed to be very deep. In another cross-section, the parallel-layered large pore seemed to be connected by many thin fibers. Sample No. 28 had a very porous structure that showed cross-layered pore pattern on one face and a puffy loose parallel fiber structure on the other. Sample No. 29 had a porous structure that resembled the pattern of fish scales on one face and layered sheets on the other. Sample No. 30 had a porous structure that seemed to be intertwined on one face and parallelly aligned on the other. Sample No. 31 had the structural features of parallel layers and honeycomb-like pores. Sample No. 32 had a loose layered structural feature on one face and a more densely packed layer structure on the other face.

The structural features of samples hydrated in pH 1 solution were generally similar to those observed with samples hydrated in pH 7 solution, although the pore size seemed to be smaller (for example, comparing pore size of Sample No. 25 at pH 7 and pH 1). These analyses strongly suggest that the structural features observed were stable under different conditions and that the highly reproducible structural features were likely an intrinsic property of each composite natural polysaccharide.

Example 23

This example demonstrates the scanning electron microscopic imaging (SEM) analysis of hydrated samples prepared by freeze drying. The samples were prepared by freeze drying (see the last two columns of Table 3). Briefly, the samples were prepared by weighing each ingredient and adding to deionized water at the ratio and mass concentration as indicated in Table 3, heating to 100° C. and stirring until all ingredients were fully dissolved. Each solution was cooled to 20° C. and stored in a 20° C. incubator for 6 hours, to form a stable gel. After 6 hours, the samples were transferred to a −20° C. freezer to store for 10 hours, thereby to obtain a cryo-stabilized gel. After 10 hours, the cryo-stabilized gel was pre-frozen until its center reached −40° C. and subjected to lyophilization. The sample was kept below −10° C. throughout the lyophilization process until the sample was dry.

To capture the structural features in the hydrated state of freeze-dried samples from Table 3 (last two columns), sample particles were soaked in deionized water (pH=7) for more than 12 hours, flash frozen in liquid nitrogen, and lyophilized to dry, sputter coated with platinum and imaged on a JOEL JSM-7001 Scanning electron microscope. For each sample, a number of particles were imaged, images most representative of the observed structural features of a given sample are shown.

Sample No. 22 from freeze drying had a relatively dense structure with some layered structural feature at the surface, which could be responsible for a certain level of water absorption observed with this sample. Sample No. 23 from freeze drying showed a cross-layered pore structure; when viewed at the cross-section the interconnected pore structure was apparent. Sample No. 23 shows a fibrous pore structure from a different perspective. Sample 24 from freeze-drying showed a fine parallel-layered structure on the surface. The cut cross-section shows that each layer contained a network of pores. Sample 25 from freeze drying showed a parallel-layered structure on the surface. The zoomed-in view showed that each layer contained a network of pores that were approximately 1-5 μm wide, and 5-10 μm long, these pores were interconnected and intertwined with each other. Sample No. 26 from freeze drying showed a very porous structure, but the pore structural pattern was less well-defined. Its surface did show a pattern of cross-layered pores. Sample No. 27 from freeze drying showed a characteristic interconnected pore pattern. The parallel-layered was also apparent on the surface. Overall, the structural features and pore pattern of freeze-dried samples in this example were similar to those observed for corresponding samples prepared by thawing-drying, although the pore sizes and the overall dry volume of the samples prepared by freeze drying were larger than their counterparts prepared by thawing drying, especially for Sample Nos. 22-25.

IN VITRO EXAMPLES

Example 24: Experimental Setup

Experiments were conducted in vitro to determine glucose bioaccessibility. Four (4) duplicate experiments were performed to test the potential reduction in meal digestion upon ingestion of the test product (e.g., Product A: Example 7, Sample 11): 2 duplicate TIM-1 experiments in dialyzer settings without test product; 2 duplicate TIM-1 experiments in dialyzer settings with test product; 2 duplicate TIM-1 experiments in filter settings without test product; and 2 duplicate TIM-1 experiments in filter settings with test product.

The aim of this experiment was to determine the bioaccessibility of macronutrients to assess the binding capacity of Product A for fat, carbohydrates, and proteins when co-administered with a meal, during transit through a dynamic, computer-controlled model of the stomach and small intestine (TIM-1). The binding capacity of Product A for protein and carbohydrate was investigated in phase Ia and for fat in phase Ib.

The TNO in vitro gastrointestinal models (i.e., TIM models) simulate in high degree the successive dynamic processes in the stomach, the small intestine, and in the large intestine. The system has been described in detail in several publications: Minekus et al., 1995 and 2005, Bellmann et al., 2014, Domoto et al., 2013, Helbig et al., 2013, and Van Loo-Bouwman et al., 2014, which are incorporated herein by specific reference in their entirety. The TIM-1 system is composed of a stomach compartment and three small intestinal compartments: the duodenum, jejunum, and ileum. Each compartment is composed of two glass units with a flexible silicone inner wall enclosing the luminal material. The space between the inner and outer walls is filled with water. Peristaltic mixing of the chyme is the result of alternate compression and relaxation of the flexible inner wall. The compartments are connected by peristaltic valve pumps that successively open and close, allowing the chyme to transit over time through the compartments. In this way, test products are exposed to locally changing and physiological relevant conditions in the stomach and the three parts of the small intestine. This makes the system a tool to study the stability, release, dissolution, absorption and bioconversion of nutrients, chemicals, bioactive compounds, and pharmaceuticals in the gastrointestinal tract.

During the experiments, the digested and dissolved molecules are dialyzed from the intestinal lumen through a semipermeable membrane unit connected to the jejunal and ileal compartment. This allows sampling during the digestion process and the assessment of the bioaccessible fraction in the dialysate. The dialyzed nutrients represent the compounds that are available for intestinal absorption (bioaccessible fraction) after digestion.

The test Product A contains granules (in the range of 400-800 μm). The granules are released and can then transition into the gastrointestinal tract freely. While doing so, they are expected to expand when meeting increased pH values. A standard meal matrix was used consisting of egg powder and mashed potato powder mix. The meal contains approximately 40 energy % fat, 21 energy % protein and 39 energy % in the form of carbohydrates. The prepared meal matrix (including electrolytes) was introduced into the stomach compartment in one step, where it is exposed to gastric enzymes (e.g., lipase, pepsin, and amylase) and gastric acid. During gradual emptying following a gastric emptying curve, the meal matrix transit towards the small intestinal compartment (e.g., duodenum), where bile, pancreatic juices, and bicarbonate were added. After 80 minutes, 50% of the gastric intake reached the duodenum.

Average test conditions (healthy human adult) after the intake of a meal were simulated. This includes among others the (postprandial) parameters like gastric emptying, the concentration of secreted bile, pancreatic juice and enzymes, pH profile in the stomach, and pH set points in the small intestinal compartments (Table 4). Prior to the performance of each experiment the secretion fluids (e.g. gastric juice with enzymes, electrolytes, bile, and pancreatic juice) were freshly prepared, the pH electrodes calibrated, and semipermeable membrane (hollow fiber) units installed.

TABLE 4

Parameters simulated in the TIM-1, describing the average gastrointestinal physiological conditions of healthy young adults

| Gastric compartment TIM-1 | |
|---|---|
| Intake (total) | 300 ml |
| Meal (standard meal) | 265.5 g |
| Water and artificial saliva | 34.5 g |
| Gastric start fluid | 10 g |
| Gastric emptying T½ | 80 min |
| House keeper wave | 180 min |
| Gastric pH | 6.5 to 1.7 in 210 min |
| Small intestinal compartment TIM-1 | |
| pH duodenum | 5.9 |
| pH jejunum | 6.5 |
| pH ileum | 7.4 |

Nitrogen (Kjeldahl) Analysis

Sample analysis were performed by using the Kjeldahl method for total nitrogen. The samples were digested using a block digestion. Concentrated sulfuric acid was used to convert protein nitrogen to ammonium sulphate at a boiling point elevated by the addition of potassium sulphate. A copper catalyst was used to enhance the reaction rate. An excess of sodium hydroxide was added to the cooled digest to liberate ammonia. The liberated ammonia was distilled into an excess of boric acid solution, using a fully automatic steam distillation unit. The automatic titration of the ammonia was carried out simultaneously with the distillation and the endpoint of the titration can also be detected by means of a potentiometric pH system. The nitrogen content was calculated from the amount of ammonia produced.

Carbohydrate Analysis

Total glucose was measured photometrically after acid hydrolysis.

Total Fatty Acids

The intake samples were digested by boiling with dilute hydrochloric acid. The hot digest was filtered through a wetted filter paper to retain fatty substances, then the fat was extracted from the dried filter paper using light petroleum.

The solvent was removed by distillation or evaporation and the substances were extracted and weighed. The samples were saponified with methanolic sodium hydroxide and then derivatized with methanolic boron trifluoride solution to their methyl esters. The methyl esters were analyzed on a gas chromatography (GC) cold on-column injection system with a flame ionization detector (FID). Heptadecanoic acid was used as an internal standard, which has a response factor of 1 relative to the compounds of interest.

Calculations

The bioaccessible fractions were calculated by multiplying the dialysate sample volume with the analyzed nitrogen/carbohydrate/TFA concentration of each sample (Equation 1).

$$BA[mg] = \frac{V[mL] \times c\left[\frac{mg}{L}\right]}{1000} \quad \text{(Equation 1)}$$

The recovery (mass balance) was calculated by the measured absolute amounts (mg) of all sample fractions (Equation 2). The recovery is used as a quality measure for all experiments and should be >80%. Equation 2 is as follows:

$$Recovery[\%] = \frac{\text{(Dialysate/filrate jejunum+ ileum}_{t=0-360}\text{ +}}{\text{Gastric residue+ Small intestinal residue)}}{\text{Input}_{endogenous+exogenous\ fractions}} \times 100\%$$

Bioaccessibility was calculated with Equation 3 as follows:

$$[\% \text{ of input}] = \frac{\text{(Dialysate/filrate jejunum+ ileum}_t\text{)}}{\text{Input}_{endogenous+exogenous\ fractions}} \times 100\% \quad (3)$$

Example 25: Glucose Bioaccessibility

To assess the effect of the test product on the bioaccessibility of glucose from the test meal, total glucose was measured in the dialysate fractions of jejunum and ileum. The total bioaccessibility (jejunum+ileum) with the test product was 75.2±1.4% of input (avg±sd, n=2) compared to 83.2±0.3% of input (avg±sd, n=2) without test product. FIG. 1 shows the cumulative small intestinal bioaccessibility. Most glucose became bioaccessible in the jejunum with amounts comparable for control and test product (60.6±0.3% and 60.1±1.0% of input for control and test product, respectively). While the bioaccessibility of glucose from the jejunum was not different between test conditions, bioaccessibility from the ileum was lower in experiments with test product (14.3±0.3% of input) compared to experiments without test product (22.6±0.6% of input).

Figure 2:
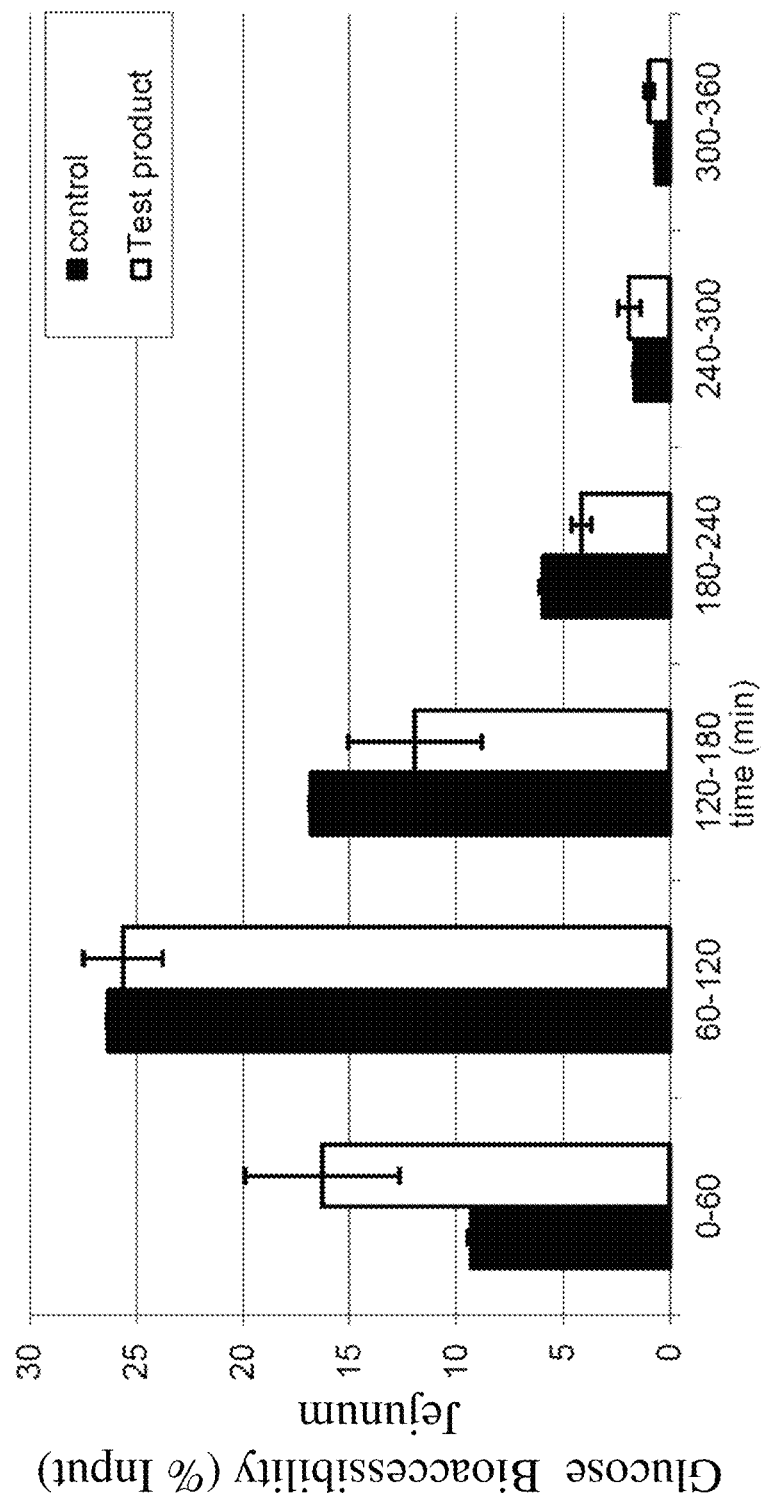
FIG. 2 includes a graph of data that shows bioaccessibility of total glucose from in vitro jejunum with and without the superabsorbent material.
Figure 3:
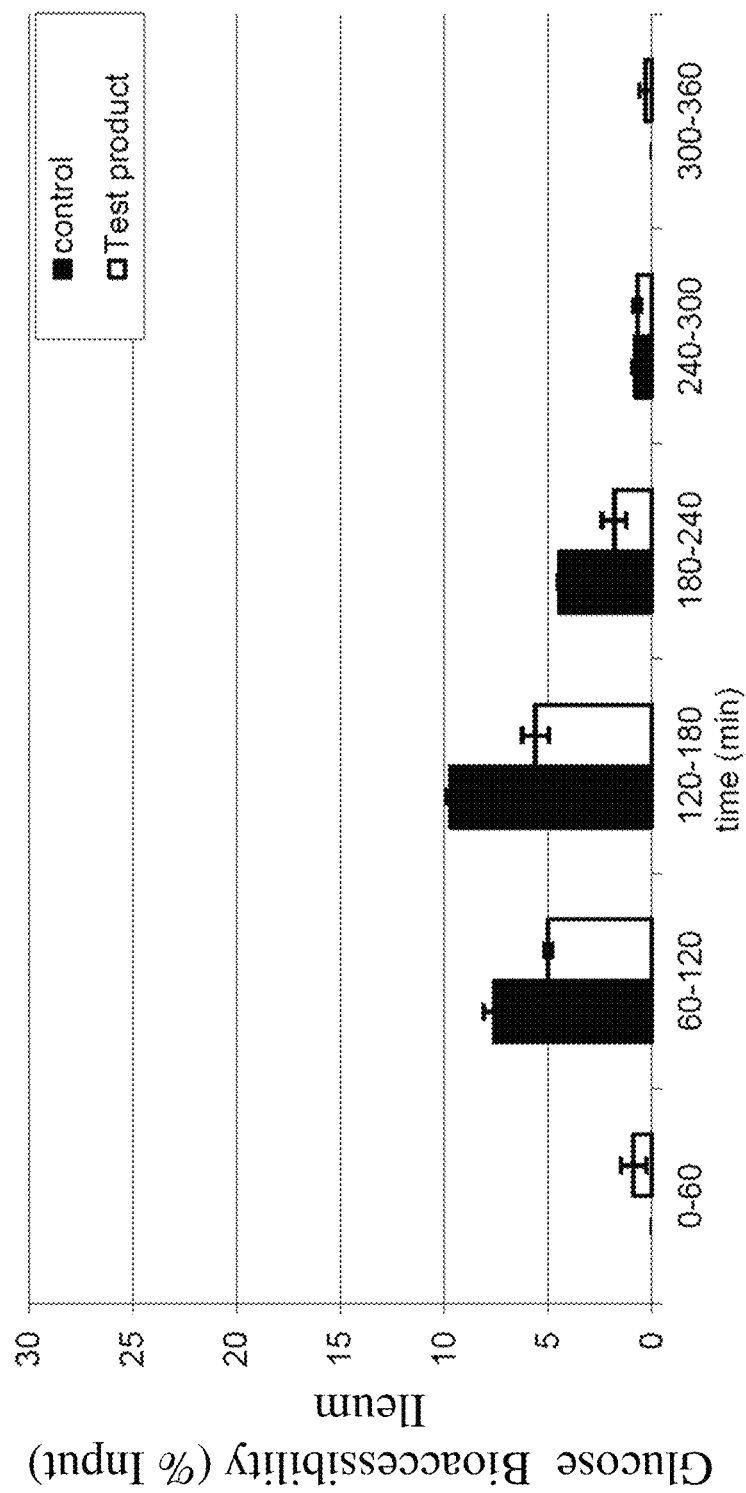
FIG. 3 includes a graph of data that shows bioaccessibility of total glucose from in vitro ileum with and without the superabsorbent material.

FIGS. 2 and 3 show the bioaccessibility for jejunum and ileum, respectively, over time. Interestingly, during the first 60 minutes of experiment, more total glucose became bioaccessible when the test meal was administered together with the test product compared to experiments without test product. Thereafter the bioaccessibility of glucose was lower (120-240 min.)/comparable in experiments with test product compared to the experiment without test product. The bioaccessibility of glucose in the ileum was higher in the first 60 minutes and lower between 60 and 240 minutes in experiments with test product compared to experiments without test product.

Recovery of total glucose was calculated from all measured sample fractions in TIM. The recovery (see Equation 2) of total glucose was 92.8±0.5 of input without test product and 82.3±1.3% of input with test product.

Example 26: Nitrogen Bioaccessibility

To assess the effect of the test product on the bioaccessibility of protein from the test meal, nitrogen was measured in the dialysate fractions of jejunum and ileum.

Figure 4:
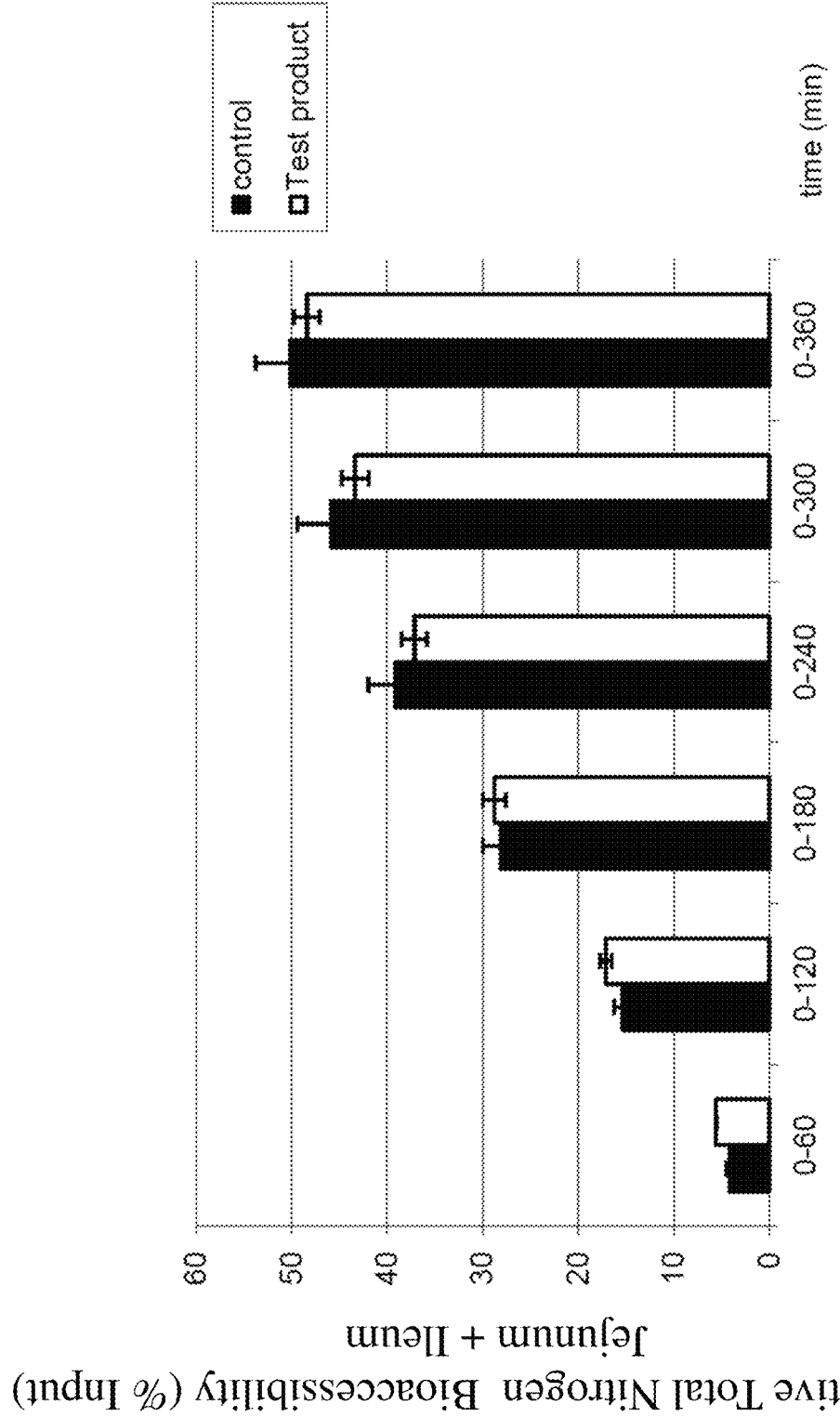
FIG. 4 includes a graph of data that shows the cumulative bioaccessibility of total nitrogen (protein) from simulated in vitro jejunum and ileum with and without the superabsorbent material.

The total bioaccessibility (jejunum+ileum) of nitrogen with test product was 48.4±1.3% of input (avg±sd, n=2) compared to 50.1±3.7% of input (avg±sd, n=2) without test product. FIG. 4 shows the cumulative small intestinal bioaccessibility. Most nitrogen became bioaccessible in the jejunum and was slightly higher for experiments with test product compared to control (34.4±1.6% of input with test product vs. 31.9±2.1% of input control). For ileum, the bioaccessibility was lower in experiments with test product (14.1±1.6% of input) compared to experiments without test product (18.2±1.6% of input).

Figure 5:
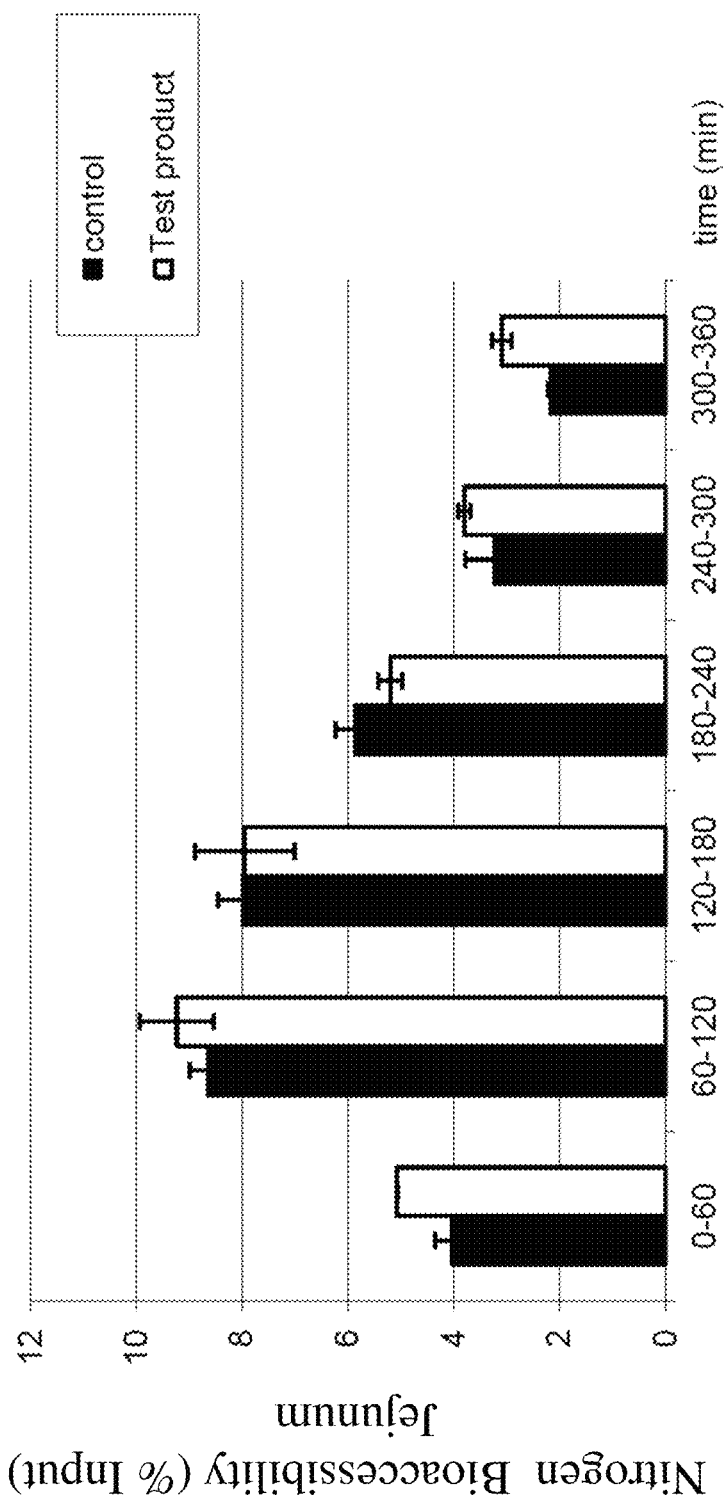
FIG. 5 includes a graph of data that shows bioaccessibility of total nitrogen (protein) from in vitro jejunum with and without the superabsorbent material.
Figure 6:
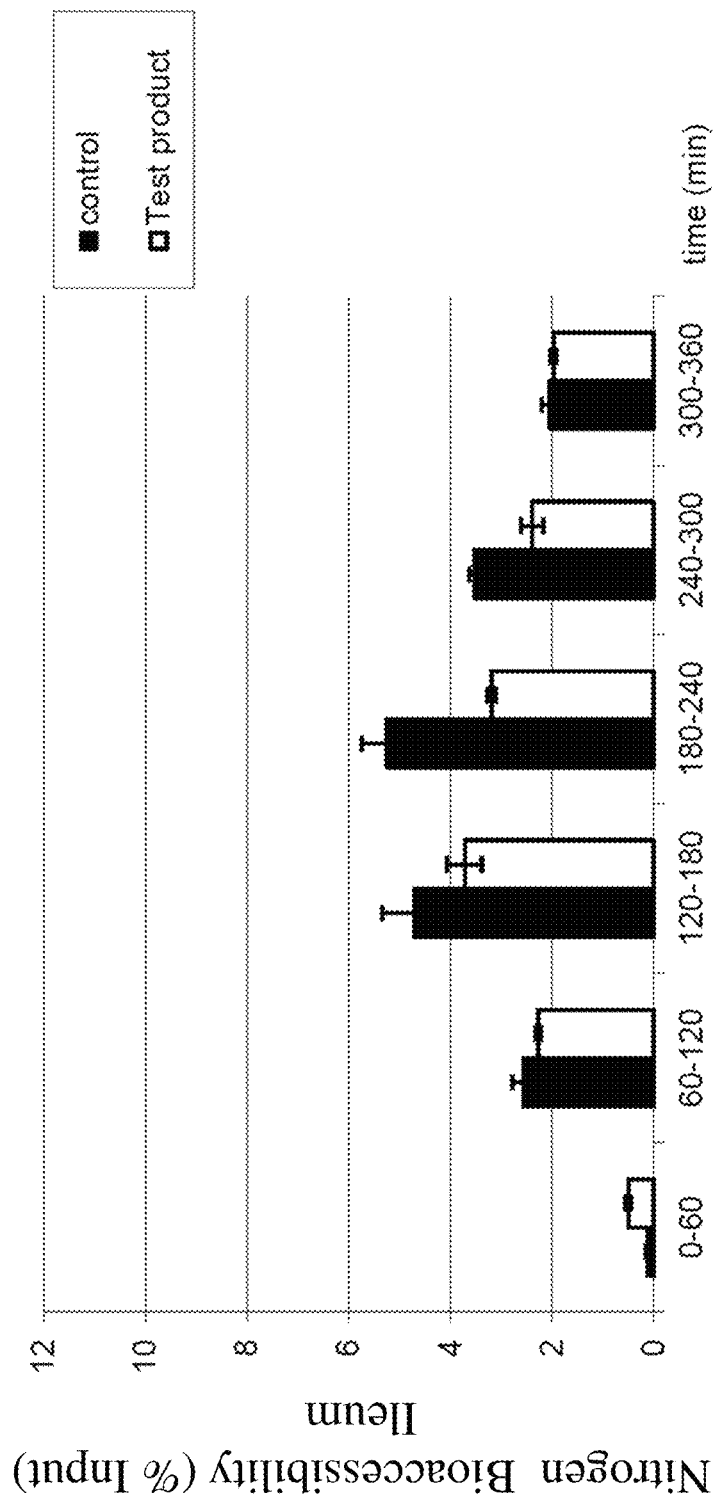
FIG. 6 includes a graph of data that shows bioaccessibility of total nitrogen (protein) from in vitro ileum with and without the superabsorbent material.

FIGS. 5 and 6 show the bioaccessibility for jejunum and ileum over time. During the first (and last) 60 min. of experiment, the nitrogen (jejunum) bioaccessibility was higher from the test meal co-administered with test product compared to the meal without test product (FIG. 5). The (ileum) bioaccessibility was lower in experiments with test product between 60 min. and 300 min. compared to experiments without test product (FIG. 6).

Recovery of nitrogen was calculated from all measured sample fractions in TIM. The recovery (Eq. 2) of nitrogen was 80.1±3.8% of input without test product and 78.8±0.9% of input with test product.

Example 27: Fatty Acid Bioaccessibility

To assess the effect of the test product on the bioaccessibility of total fatty acids from the test meal, TFA were measured in the filtrate fractions of jejunum and ileum.

Figure 7:
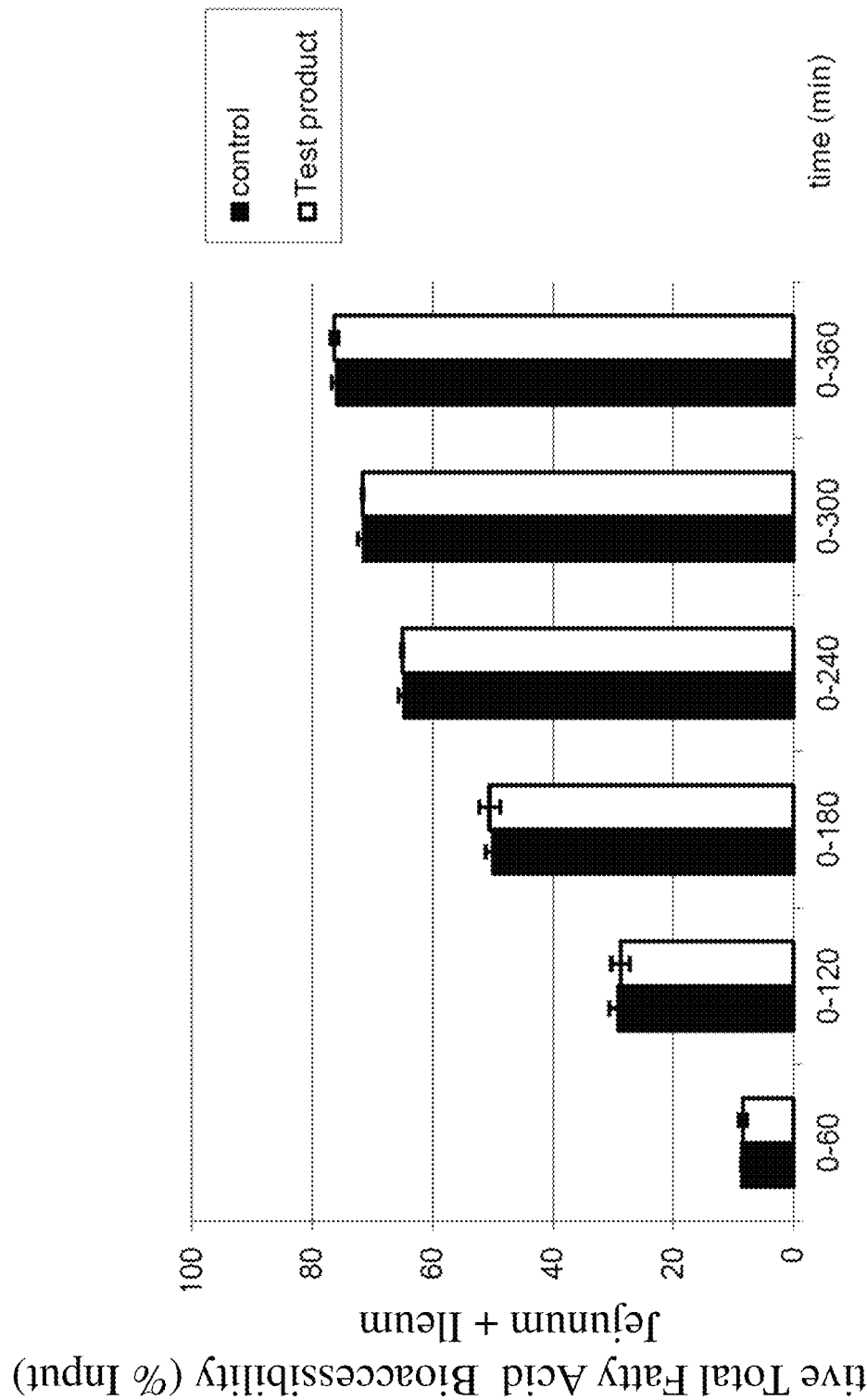
FIG. 7 includes a graph of data that shows the cumulative bioaccessibility of total fatty acid (TFA) from simulated in vitro jejunum and ileum with and without the superabsorbent material.

The total bioaccessibility (jejunum+ileum) with test product was 76.4±0.6% of input (avg±sd, n=2) compared to 75.9±0.8% of input (avg±sd, n=2) without test product. FIG. 7 shows the cumulative small intestinal bioaccessibility. Most TFA became bioaccessible in the jejunum and was comparable between the test conditions (56.1±0.0% of input control and 56.3±0.3% of input with test product). Similarly, for ileum, bioaccessibility of TFA was comparable between the test conditions (19.9±0.8% of input control and 20.1±0.3% of input with test product).

Figure 8:
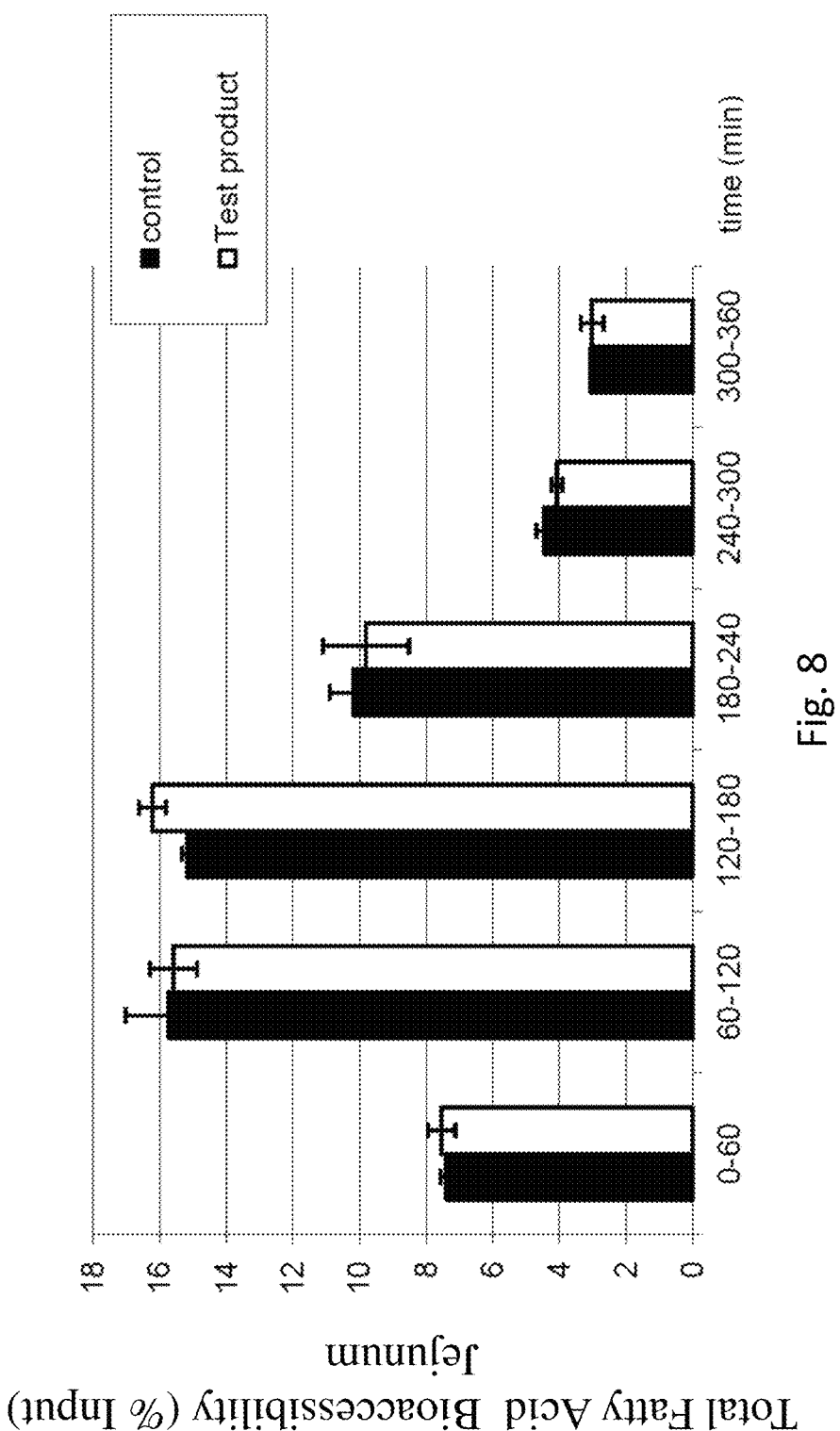
FIG. 8 includes a graph of data that shows bioaccessibility of total fatty acid (TFA) from in vitro jejunum with and without the superabsorbent material.
Figure 9:
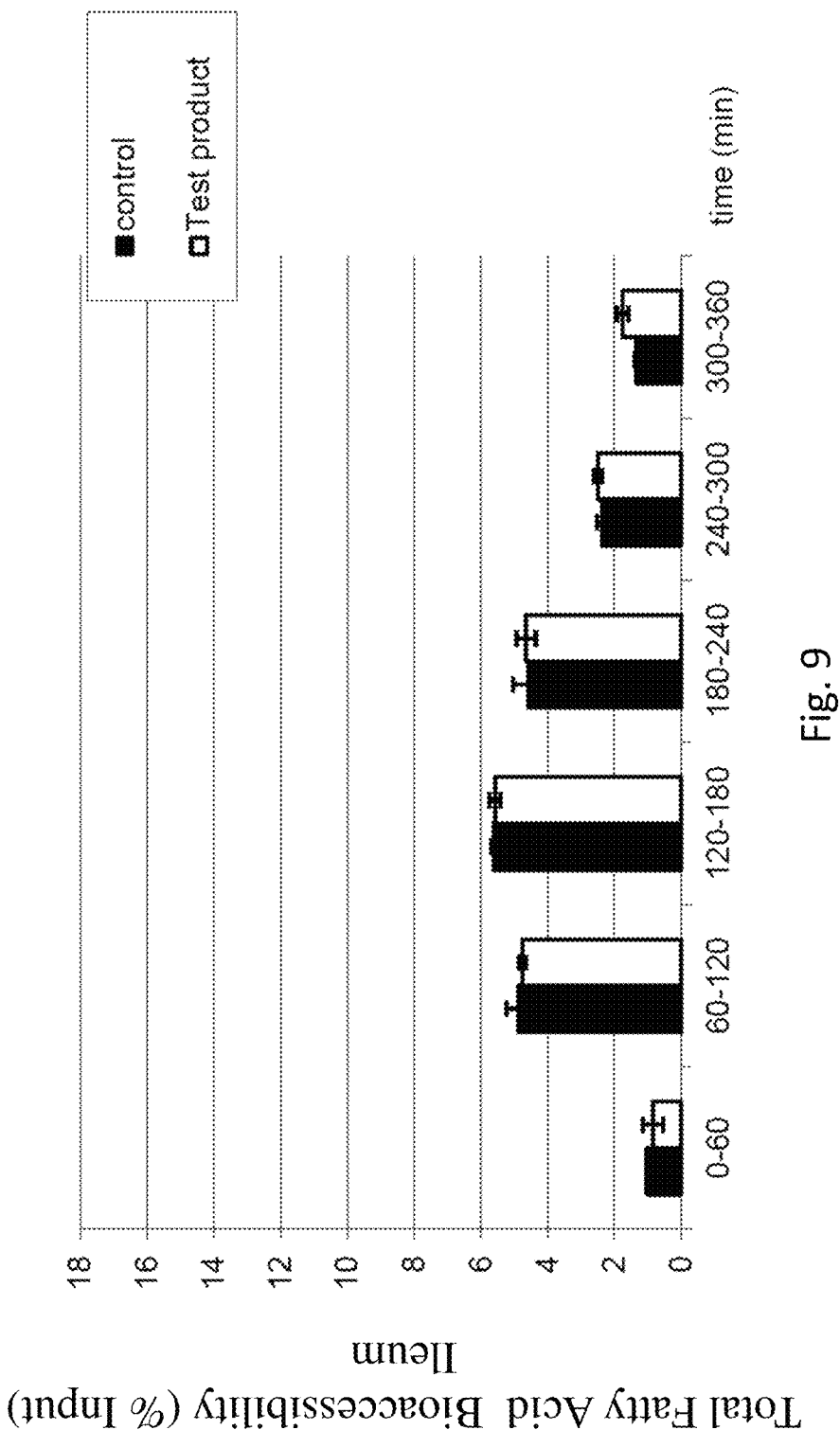
FIG. 9 includes a graph of data that shows bioaccessibility of total fatty acid (TFA) from in vitro ileum with and without the superabsorbent material.

FIGS. 8 and 9 show the TFA bioaccessibility for jejunum and ilium, respectively over time. The bioaccessibility was comparable between test conditions, except for sample fraction 120-180 min. In this time period, the TFA bioaccessibility was slightly higher for experiments with test product (16.2±0.4% of input) compared to experiments without test product (15.2±0.1% of input). For ileum, the TFA bioaccessibility was largely comparable. Only the last 60 min, the TFA bioaccessibility was higher for experiments with test product (1.8±0.2% of input) compared to without test product (1.3±0.1% of input) (FIG. 9).

Recovery of TFA was calculated from all measured sample fractions in TIM. The recovery (Eq. 2) of TFA was 103.5±0.5% of input for control and 103.6±1.0% of input with test product.

IN VIVO EXAMPLES

Example 28: Materials and Methods

Experiments were conducted to determine the effect of the superabsorbent material for an obesity treatment. The superabsorbent material was studied in a diet-induced obesity (DIO) mouse model to determine changes in food intake, bodyweight, lipids, glucose, insulin, insulin sensitivity, leptin, gastrointestinal function, and other parameters as described herein.

Mouse Model

A mouse model for obesity and diabetes was obtained and used in the studies. The mouse model was the C57Bl/6 mouse, where the mice were obtained from Jackson Lab at age 6-7 weeks and a weight of about 25-30 grams. Seven days of acclimation time was applied to the mice. The mice were housed in a ventilated cage rack system on a 12 hour light/dark cycle (lights on 7:00 AM). There were 4 mice per cage. Standard rodent chow and water were provided to the mice ad libitum, which included 60% kcal high-fat diet (HFD; Research Diet D12492, pellet).

Test Groups

The superabsorbent material was prepared into the mouse feed. The superabsorbent material was formulated with the high-fat diet and delivered to the test mice in the same manner as the HFD treatment was provided. For example, 25 mg of superabsorbent material (e.g., Product A: Example 7, Sample 11) was provided for consumption per day for each mouse for a period of 8 weeks. After seven days of acclimation, the mice were randomized into different groups based on bodyweights. The mice were divided into groups, each group having 10 mice based on the groups with the same diets: (Group 1) Standard Diet (e.g., standard rodent chew diet), (Group 2) High-fat Diet (HFD), and (Group 3) High-fat Diet and Treatment 1 (HFD+product A). The mice were dosed with the test diets of the different groups. The dosing of test diets began on day 1 at the same time as the food induction and the study duration was 56 days.

Weekly Data Acquisition

The mice were treated with the test diets for a period of weeks. During the test period, the two-hour fasting blood glucose and body weights were measured once a week. The food intake was measured twice a week: on Monday by weighing food that was placed in the cage-top hopper; and on Friday by weighing the leftover food.

Oral Glucose Tolerance Test

In week 7-8, an oral glucose tolerance test (OGTT) was conducted to assess insulin sensitivity changes. During OGTT, mice were bled for baseline glucose at time 0 and then administered a glucose solution (2 g/kg) via oral gavage administration. After the glucose challenge, blood glucose levels were measured according to the schedule. Blood glucose levels were measured using Glucocard Vital glucometers (Arkray, Minneapolis, MN) and levels reported as mg/dL. Glucometers were calibrated prior to each study. Blood (<5 µL) was acquired from a tail snip and directly applied to a glucose test strip.

Fecal Output Test

At the end of the study, mice were fed ad libitum until the acclimation period. Then mice were weighed, singly housed in polyurethane cages without access to food, and acclimated to the procedure room at least 30 minutes prior to the study. At each subsequent hour after administration up to 4 hours, the number of fecal pellets per animal and the weight of all fecal pellets produced per animal in each hour period were recorded. All collected fecal samples were snap frozen and stored at −80° C.

Example 29: Body Weight

The mice were weighed weekly as indicated, the bodyweight of all mice were recorded for the entire study. FIG. 1 includes a graph of data that shows the bodyweight in grams per day for the mice in the study, where the mice are in groups based on the diets: (Group 1) Standard Diet (e.g., standard rodent chew diet), (Group 2) High-fat Diet (HFD), and (Group 3) High-fat Diet and Treatment 1 (HFD+Product A). The bodyweight change percentage is calculated as (bodyweight change)/(baseline bodyweight)×100. Compared to the standard diet-fed control mice of Group 1, the high fat diet (HFD) treated mice of Group 2 showed significantly higher bodyweight change percentage after about Day 12. The bodyweight in grams is shown per day is shown in FIG. 1. For the first 12 days, the weights were relatively similar; however, Day 12 marked a divergence where Group 2 mice started significantly faster weight gains. Compared with the HFD treated mice of Group 2, the Product A (HFD-PA) treated mice of Group 3 displayed significantly lower bodyweight change percentage after Day 22. The data suggests that the superabsorbent material of Product A can prevent or reduce high fat diet induced bodyweight gain. Data are mean±SEM and analyzed by two-way ANOVA as applicable (compared to HFD-Vehicle, n=10-14/group).

Example 30: Insulin Levels

Figure 11:
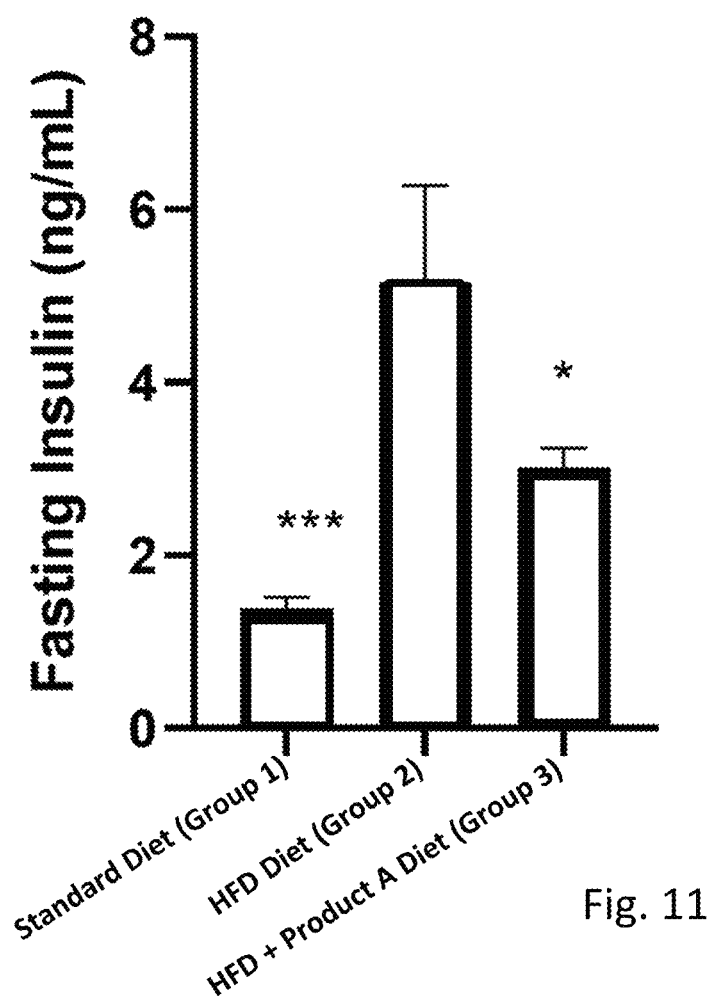
FIG. 11 includes a graph of data that shows the fasting insulin levels for Group 1 (standard diet), Group 2 (HFD treatment), and Group 3 (HFD+Product A treatment).

The fasting insulin levels were analyzed as described. The blood insulin profile was assessed at the end of the study under fasting condition. FIG. 11 shows the fasting insulin levels for Group 1 (standard diet), Group 2 (HFD treatment), and Group 3 (HFD+Product A treatment). As shown, the HFD treatment significantly increases the insulin level in the mice. This increase with the HFD treatment had significantly higher levels of insulin, which is consistent with insulin resistance/hyperinsulinemia status attributed to the high calorie diet. However, the addition of Product A in the Group 3 mice shows a decrease in the insulin level. Compared to the Group 2 mice, the Group 3 mice displayed significant reductions in insulin levels. Data are mean±SEM and analyzed by In FIG. 11, one-way ANOVA as applicable (compared to HFD-Vehicle, n=10-14/group), with **: $p<0.0001$; :$p<0.01$;*$p<0.05$ vs. Group 2. This shows that the Product A can inhibit the increase of insulin attributed to the HFD treatment. As such, the amount of insulin can be reduced by providing the Product A, especially in HFD diets.

Example 31: Leptin Levels

Figure 12:
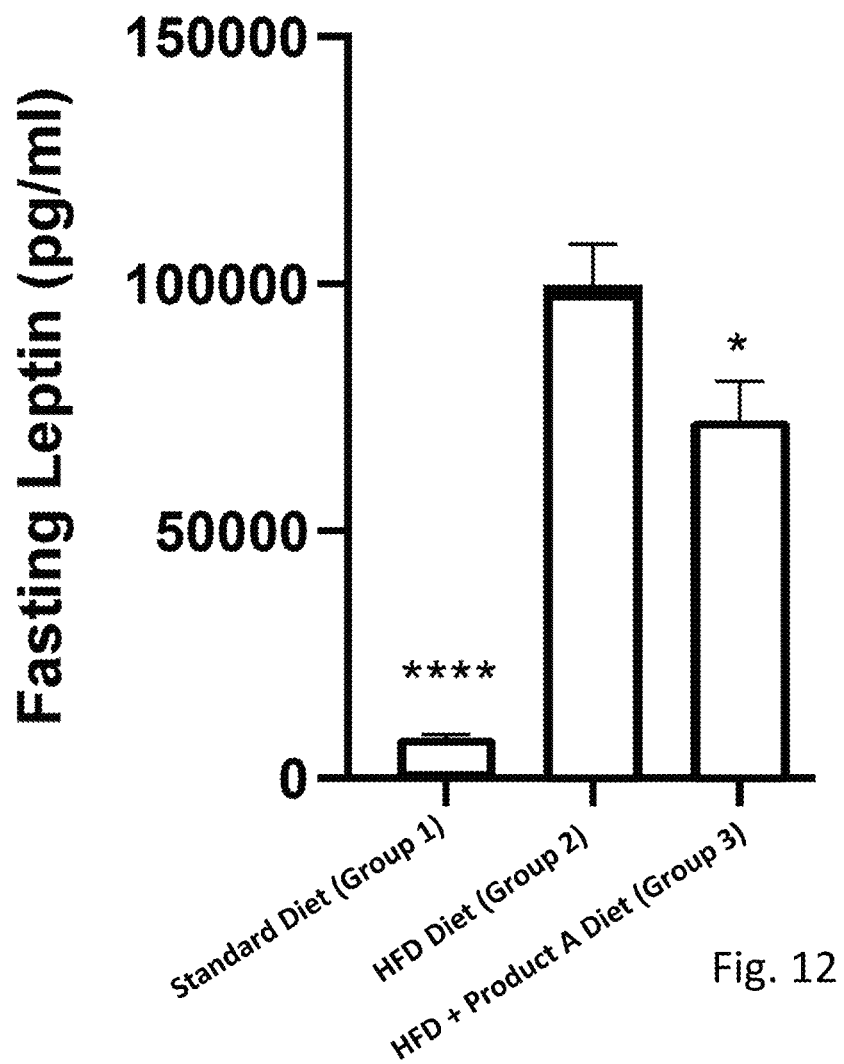
FIG. 12 includes a graph of data that shows the fasting leptin levels for Group 1 (standard diet), Group 2 (HFD treatment), and Group 3 (HFD+Product A treatment).

The fasting leptin levels were analyzed as described. The blood leptin profile was assessed at the end of the study under fasting condition. FIG. 12 shows the fasting leptin levels for Group 1 (standard diet), Group 2 (HFD treatment), and Group 3 (HFD+Product A treatment). As shown, the HFD treatment significantly increases the leptin level in the mice. This increase with the HFD treatment had significantly higher levels of leptin, which is consistent with leptin resistance/hyperleptinemia status attributed to the high calorie diet. However, the addition of Product A in the Group 3 mice shows a decrease in the leptin level. Compared to the Group 2 mice, the Group 3 mice displayed significant reductions in leptin levels. Data are mean±SEM and analyzed by One-way ANOVA as applicable (compared to HFD-Vehicle, n=10-14/group), in FIG. 12 **:p<0.0001; :p<0.01;*p<0.05 vs. Group 2. This shows that the Product A can inhibit the increase of leptin attributed to the HFD treatment. As such, the amount of leptin can be reduced by providing the Product A, especially in HFD diets.

Example 32: HOMA-IR Levels

Figure 13:
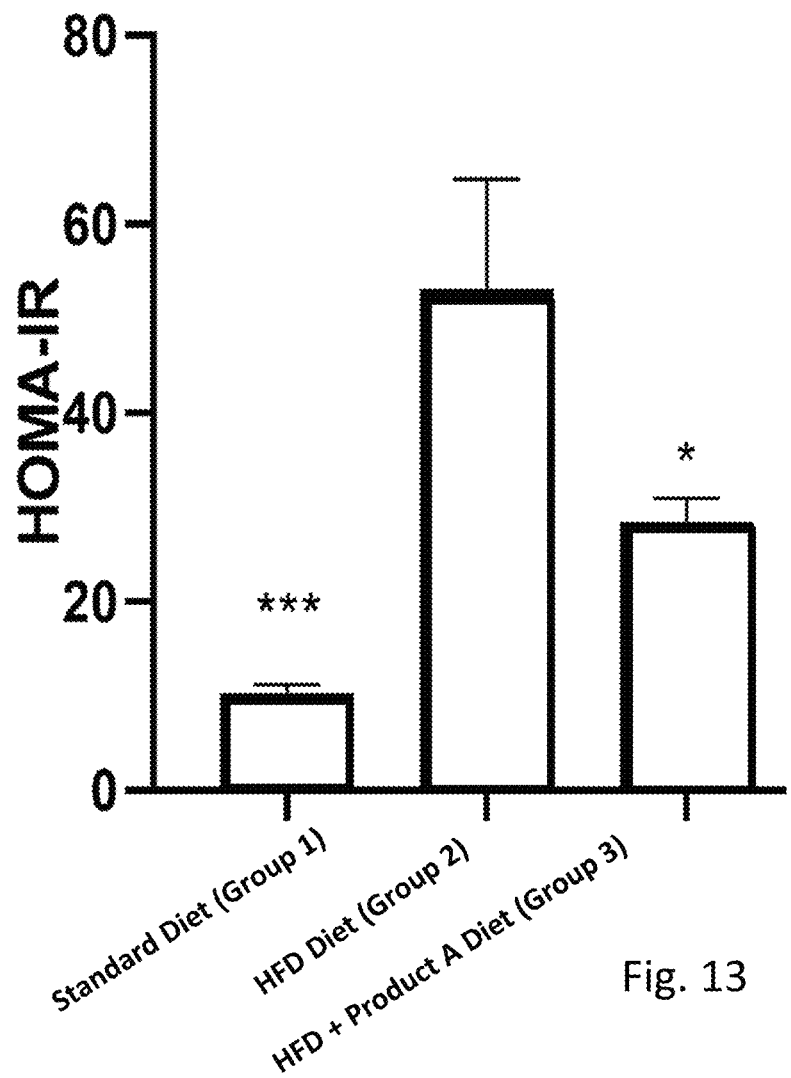
FIG. 13 includes a graph of data that shows the HOMA-IR levels for Group 1 (standard diet), Group 2 (HFD treatment), and Group 3 (HFD+Product A treatment).

The fasting glucose and insulin levels were analyzed as described. The homeostatic model assessment (HOMA) is a method used to quantify insulin resistance and beta-cell function. The HOMA-IR equals (glucose×insulin)/22.5. Here, IR indicates insulin resistance, and the measurements are taken for fasting glucose and fasting insulin. The higher the HOMA-IR, the higher the insulin resistance, and lower the HOMA-IR, the lower the insulin resistance. The blood glucose and insulin profiles were assessed at the end of the study under fasting condition. FIG. 13 shows the fasting HOMA-IR levels for Group 1 (standard diet), Group 2 (HFD treatment), and Group 3 (HFD+Product A treatment). As shown, the HFD treatment significantly increases the HOMA-IR level in the mice. This increase with the HFD treatment had significantly higher levels of HOMA-IR, which is consistent with insulin resistance. However, the addition of Product A in the Group 3 mice shows a decrease in the HOMA-IR level, and thereby a decrease in insulin resistance. Compared to the Group 2 mice, the Group 3 mice displayed significant reductions in HOMA-IR levels. Data are mean±SEM and analyzed by One-way ANOVA as applicable (compared to HFD-Vehicle, n=10-14/group), in FIG. 13 **:p<0.0001; :p<0.01;*p<0.05 vs. Group 2. This shows that the Product A can inhibit the increase of insulin resistance attributed to the HFD treatment. As such, the amount of insulin resistance can be reduced by providing the Product A, especially in HFD diets.

One skilled in the art will appreciate that, for the processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

As used herein, "prevent" or "prevented" or "preventing" or "prevention" refer to prevention or delay of the onset of a disorder, disease, or condition associated with high glucose bioaccessibility and bioavailability (e.g., insulin resistance, diabetes, obesity, etc.) and/or a decrease in the symptoms in a subject relative to the symptoms of diseases associated with high glucose that would develop in the absence of the methods of the invention. The prevention can be complete, for example, the total absence of high glucose or condition thereof in a subject that undergoes the treatment with the superabsorbent material described herein. The prevention of high glucose bioaccessibility and disease states associated therewith can also be partial, such that the lower glucose level in a subject has reduced symptoms from that which would have occurred without the present invention. The terms "prevention", "prophylactic treatment", and "prophylaxis" may be used interchangeable and are intended to refer to prevention.

The term "administered," "administering" or "administration" includes routes of administration which allow the superabsorbent material to perform their intended function (s) of reducing glucose bioaccessibility and thereby preventing, mitigating, or treating a disease associated with high glucose bioavailability in a subject, which can include oral consumption of the superabsorbent material. However, it may be possible that the superabsorbent material is formulated in a pharmaceutical composition for routes of administration other than oral consumption.

When used herein, the term "therapeutically effective amount" or "effective amount" includes an amount of the therapeutic or treatment composition that provides a prophylactic or therapeutic benefit in the treatment, prevention, or management of a disease or a symptom of a disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The term "therapeutically effective amount" or "effective amount" of the superabsorbent material includes an amount of the superabsorbent material that is sufficient in treating, mitigating, or preventing high glucose bioaccessibility and/or bioavailability. Alternatively, an "effective amount" of the superabsorbent material means an amount of the superabsorbent material to be administered necessary to treat or prevent a disease or disorder mediated by high glucose bioaccessibility and/or bioavailability.

A therapeutically effective amount can be readily determined on an individual basis and will be based, in part, on the severity of high glucose bioaccessibility and/or bioavailability. Thus, a therapeutically effective amount of superabsorbent material can be determined by one of ordinary skill in the art using no more than routine experimentation in clinical management of a subject. For example, the specific amount that is therapeutically effective may be readily determined by ordinary medical practitioner, and may vary depending on factors known in the art, such as, e.g. the type and location of infection, the patient's history (including genetic and medical history), sex, age, the patient's family history (including genetic and medical history), the patient's history of high glucose bioaccessibility and/or bioavailability, and the current administration of other therapeutic agents. Another factor influencing clinical management of a subject is the patient's side effect profile history. For example, a glucose or otherwise high caloric diet may influence the determination of a specific treatment regimen of a subject in need of treatment, mitigation, or prevention of obesity or insulin resistance.

The dosage ranges for the administration of are those that produce the desired effect. Generally, the dosage will vary with the age, weight, condition, and sex of the patient, and the extent of disease. A person of ordinary skill in the art, given the teachings of the present specification, may readily determine suitable dosage ranges.

In some embodiments, a therapeutically effective amount of the superabsorbent material includes a precise dosage level determined by an attending physician or other health care provider and will depend upon well-known factors, including route of administration, and the age, body weight, sex, concomitant therapies, patient medical history including previous drug tolerances, general health of the patient; the nature, severity and clinical stage of high glucose bioaccessibility and/or bioavailability, and/or other clinical dosing factors known in the art.

The superabsorbent material can be a powder or prepared into any consumable having the powder. Also, the powder can be hydrated and gelled as described herein prior to consumption. However, an example administration is a pill or capsule of the superabsorbent material, or other suitable dosage form that may or may not include a pharmaceutically acceptable carrier.

Pharmaceutically acceptable carriers that may be useful in formulating pharmaceutical compositions of the present invention include but are not limited to lubricants, preservatives, stabilizers, solubilizers, penetrants, wetting agents, drying agents, bulking agents, fillers, emulsifiers, salts for influencing osmotic pressure, tonicity contributors (e.g., dextrose, mannitol, glycine and sodium chloride), buffers, antioxidants, colorings, flavorings and/or aromatic substances and the like which do not deleteriously react with the active compounds of the invention or each other.

Clearly, the skilled person can use other pharmaceutical formulations of the present invention containing superabsorbent materials. Pharmaceutical compositions of the present invention, and methods of forming such compositions, are described in detail by reference to standard textbooks such as Remington: The Science and Practice of Pharmacy, Twenty-Second Edition (Lippincott Williams & Wilkins, 2012); Handbook of Pharmaceutical Excipients, Seventh Edition (Pharmaceutical Press, 2012); Ansel's Pharmaceutical Dosage Forms and Drug Delivery Systems, Tenth Edition (Lippincott Williams & Wilkins, 2013); Modern Pharmaceutics, Fifth Edition (CRC Press, 2009); and in Harry's Cosmeticology, Ninth Edition (Chemical Publishing Company, 2015). Said standard textbooks are incorporated herein by reference in their entirety. Examples of suitable pharmaceutically acceptable carriers include water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, and the like. However, pure or otherwise formulated superabsorbent material can be prepared into capsules containing the powdered form.

Formulations of the superabsorbent material suitable for oral administration may be in the form of capsules, pills, wafers, tablets, lozenges, cachets, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like. In solid dosage forms for oral administration (capsules, tablets, wafers, pills, powders, granules and the like), the superabsorbent material can be mixed with one or more pharmaceutically acceptable carriers (e.g., sodium citrate, dicalcium phosphate, and/or any of the following: fillers or extenders, such as starches, lactose, sucrose, glucose, mannitol, and/or silicic acid; binders, (e.g., carboxymethylcellulose, gelatin, sucrose and acacia); humectants (e.g. glycerol); disintegrating agents (e.g. agar-agar, calcium carbonate, tapioca starch); solution-retarding agents (e.g. paraffin); absorption accelerators; wetting agents (e.g. cetyl alcohol); absorbents (e.g. kaolin); lubricants (e.g., talc, magnesium stearate, solid polyethylene glycols, sodium lauryl sulfate); and coloring agents). In the case of capsules, tablets and pills, the pharmaceutical compositions may also comprise suitable buffering agents. Solid compositions of a similar type may also be employed as fillers in soft and hard-filled gelatin or gelatin-type capsules (e.g., employing such excipients as lactose, high molecular weight polyethylene glycols, and the like).

A tablet may be made by compression or molding, optionally with one or more accessory ingredients. Compressed tablets may be prepared using binder, lubricant, inert diluent, preservative, disintegrant, and/or surface-active or dispersing agent. Molded tablets may be made, for example, by molding in a suitable machine a mixture of the powdered compound moistened with an inert liquid diluent. The tablets, and other solid dosage forms of the pharmaceutical compositions of the invention, such as capsules, pills, and granules/powders, may optionally be scored or prepared with coatings and shells, such as enteric coatings and other coatings well known in the pharmaceutical-formulating art.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

This patent application cross-references: U.S. patent application Ser. No. 17/327,020 filed May 21, 2021; U.S. patent application Ser. No. 17/327,037 filed May 21, 2021; U.S. Patent Application No. 63/205,659 filed May 21, 2021; U.S. Patent Application No. 63/205,660 filed May 21, 2021; U.S. Patent Application No. 63/205,661 filed May 21, 2021; U.S. patent application Ser. No. 16/807,004 filed Mar. 2, 2020; International Patent Application No. PCT/US2019/046077 filed Aug. 10, 2019; and U.S. Patent Application No. 62/717,644 filed Aug. 10, 2018. All references recited herein are incorporated herein by specific reference in their entirety.

The invention claimed is:

1. A method for reducing glucose bioaccessibility in a subject, comprising administering to the subject an effective amount of a superabsorbent material having a porous network structure without any chemical cross-linking; wherein the superabsorbent material is a dehydrated gel comprising agar, carrageenan, and konjac gum; and wherein the superabsorbent material has an absorption ratio of at least 10 in deionized water at 25° C.

2. The method of claim 1, wherein
the superabsorbent material is administered before, during, or after the subject has consumed a glucose-containing food or a glucose-generating food.

3. The method of claim 2, wherein the superabsorbent material is administered in an amount from about 0.01% to about 20% by weight of the consumed food.

4. The method of claim 1, wherein the superabsorbent material has an average particle size of from about 0.1 micron to 1 mm.

5. The method of claim 1, wherein the superabsorbent material is administered in an amount from about 0.1 g to about 20 g per dose.

6. The method of claim 2, wherein the glucose-generating food is a carbohydrate.

7. The method of claim 1, wherein the glucose bioaccessibility is reduced with the superabsorbent material compared to the glucose bioaccessibility without the superabsorbent material.

8. The method of claim 2, wherein the glucose bioaccessibility is reduced with the superabsorbent material compared to the glucose bioaccessibility without the superabsorbent material after about 60 minutes after the consumption of the food.

9. The method of claim 8, wherein the glucose bioaccessibility is reduced with the superabsorbent material compared to the glucose bioaccessibility without the superabsorbent material before about 140 minutes after the consumption of the food.

10. The method of claim 1, wherein the method is to inhibit an increase or reduce at least one of: the weight of the subject; fat in the subject; or a fatty liver disease in the subject.

11. The method of claim 1, wherein the method is to inhibit an increase or reduce at least one of: total cholesterol in the subject; low-density lipoprotein (LDL) in the subject; or high-density lipoprotein (HDL) in the subject.

12. The method of claim 1, wherein the method is to inhibit an increase or reduce at least one of: fasting insulin level in the subject; fasting leptin level in the subject; or a HOMA-IR value for the subject.

13. The method of claim 1, wherein the superabsorbent material comprises at least 10% by weight of agar.

14. The method of claim 1, wherein the superabsorbent material comprises at least 20% by weight of carrageenan.

15. The method of claim 1, wherein the superabsorbent material comprises agar, carrageenan, and konjac gum at a weight ratio of 10:1:1, 1:1:1, 1:1:2, 1:2:1, 2:1:1, or 2:5:5.

16. The method of claim 1, wherein the superabsorbent material comprises agar, carrageenan, and konjac gum at a weight ratio of 1:1:1, 1:1:2, or 1:2:1.

17. The method of claim 1, wherein the superabsorbent material has an absorption ratio from 20 to 200 in deionized water at 25° C.

18. The method of claim 1, wherein the superabsorbent material has an absorption ratio from 50 to 200 in deionized water at 25° C.

19. The method of claim 1, wherein the superabsorbent material has an absorption ratio from 100 to 200 in deionized water at 25° C.

* * * * *